(12) United States Patent
De Paepe et al.

(10) Patent No.: US 10,761,042 B2
(45) Date of Patent: Sep. 1, 2020

(54) METHODS AND SYSTEMS FOR CHARACTERIZING VOID FRACTIONS

(71) Applicant: UNIVERSITEIT GENT, Ghent (BE)

(72) Inventors: Michel De Paepe, Gentbrugge (BE);
Kathleen De Kerpel, Ghent (BE);
Hugo Caniere, Gentbrugge (BE)

(73) Assignee: UNIVERSITEIT GENT, Ghent (BE)

( * ) Notice: Subject to any disclaimer, the term of this patent is extended or adjusted under 35 U.S.C. 154(b) by 0 days.

(21) Appl. No.: 16/410,592

(22) Filed: May 13, 2019

(65) Prior Publication Data
US 2019/0277788 A1    Sep. 12, 2019

Related U.S. Application Data

(62) Division of application No. 14/404,666, filed as application No. PCT/EP2013/061323 on May 31, 2013, now Pat. No. 10,330,625.

(30) Foreign Application Priority Data

May 31, 2012    (EP) .................................... 12170296

(51) Int. Cl.
| | |
|---|---|
| *G01N 27/22* | (2006.01) |
| *G01N 33/28* | (2006.01) |
| *F28F 27/02* | (2006.01) |
| *G01N 33/00* | (2006.01) |

(Continued)

(52) U.S. Cl.
CPC .............. *G01N 27/22* (2013.01); *F28F 27/02* (2013.01); *G01N 33/0004* (2013.01); *G01N 33/26* (2013.01); *G01N 33/2823* (2013.01); *G01N 27/02* (2013.01)

(58) Field of Classification Search
None
See application file for complete search history.

(56) References Cited

U.S. PATENT DOCUMENTS

| | | |
|---|---|---|
| 5,287,752 A | 2/1994 | Den Boer |
| 5,855,119 A | 1/1999 | Pfister et al. |

(Continued)

FOREIGN PATENT DOCUMENTS

| | | |
|---|---|---|
| EP | 0308004 A2 | 3/1989 |
| EP | 0798533 A1 | 10/1997 |
| WO | 03029775 A2 | 4/2003 |

OTHER PUBLICATIONS

Moon-Hyun et al., "Experimental Investigation of Parametric Effects on the Void Fraction Measurement and Flow Regime Characterization by Capacitance Transducers," Journal of the Korean Nuclear Society, vol. 17, No. 1, Mar. 1985, pp. 34-44.

(Continued)

*Primary Examiner* — Syed A Roni
(74) *Attorney, Agent, or Firm* — Workman Nydegger

(57) ABSTRACT

The present invention relates to a method and system for determining the void fraction of a multi-phase system in a channel. The method comprises the steps of measuring a void fraction dependent parameter of the multi-phase system, obtaining a flow regime of the multi-phase system, and determining the void fraction of the multi-phase system taking into account a set of one or more relationships between the void fraction dependent parameter and the void fraction, the set of relationships being specific for the obtained flow regime.

16 Claims, 18 Drawing Sheets

(51) Int. Cl.
*G01N 33/26* (2006.01)
*G01N 27/02* (2006.01)

(56) References Cited

U.S. PATENT DOCUMENTS

2007/0280862 A1   12/2007   Davis et al.
2011/0259574 A1   10/2011   Angel et al.

OTHER PUBLICATIONS

Moon-Hyun et al., "Experimental Effects on the Void Fraction Measurement by Capacitance Transducers," International Journal of Multiphase Flow, vol. 12, No. 4, Jan. 1, 1986, pp. 627-640.
Ahmed et al., "Innovative Techniques for Two-Phase Flow Measurements," Recent Patents on Electrical Engineering, Jan. 1, 2008, 13 Pages.
Rocha et al., "Capacitance Sensor for Void Fraction Measurement in a Natural Circulation in a Natural Circulation Refrigeration Circuit," 2009 International Nuclear Atlantic Conference—INAC 2009, Sep. 27, 2009, 12 Pages.
Caniere et al., "Refrigerant Flow Void Fraction measurements by a Capacitance Measurement Technique," 7th International Conference on Multiphase Flow, ICMF 2010, May 30, 2010, 6 Pages.
Caniere et al., "Mapping of Horizontal Refrigerant Two-Phase Flow Patterns Based on Clustering of Capacitive Sensor Signals," International Journal of Heat and Mass Transfer, vol. 30, No. 23-24, Nov. 1, 2010, pp. 5298-5307.
Paranjape et al., "Electrical Impedance-based Void Fraction Measurement and Flow Regime Identification in Microchannel Flows Under Adiabatic Conditions," International Journal of Multiphase Flow, Feb. 27, 2012, pp. 175-183.
International Search Report from PCT Application No. PCT/EP2013/061323, dated Oct. 16, 2011.
Azzopardi, "Drops in Annular Two-Phase Flow," International Journal of Multiphase Flow, vol. 23, 1997, 53 Pages.
Caniere et al., "Capacitance Signal Analysis of Horizontal Two-Phase Flow in a Small Diameter Tube," Experimental Thermal and Fluid Science, vol. 32, 2008, pp. 892-904.
Cioncolini et al., "Prediction of the Entrained Liquid Fraction in Vertical Annular Gas-Liquid Two-Phase Flow," International Journal of Multiphase Flow, vol. 36, 2010, pp. 293-302.
Keska et al., "Comparison Study of a Cluster of Four Dynamic Flow Pattern Discrimination Techniques for Multi-Phase Flow," Flow Measurement and Instrumentation, vol. 10, 1999, pp. 65-77.
Rouhani et al., "Calculation of Void Volume Fraction in the Subcooled and Quality Boiling Regions," International Journal of Heat and Mass Transfer, vol. 13, 1970, pp. 383-393.
Schubring et al., "Critical Friction Factor Modeling of Horizontal Annular Base Film Thickness," International Journal of Multiphase Flow, vol. 35, 2009, pp. 389-397.
Wojtan et al., "Investigation of Flow Boiling in Horizontal Tubes: Part I—A New Diabetic Two-Phase Flow Pattern Map," International Journal of Heat and Mass Transfer, vol. 48, 2005, pp. 2955-2969.

(a)

(b)

(c)

METHODS AND SYSTEMS FOR CHARACTERIZING VOID FRACTIONS

FIELD OF THE INVENTION

The invention relates to the field of heat transfer systems for cooling and/or heating. More particularly, the present invention relates to methods and systems for characterizing void fractions in heat transfer systems for cooling and/or heating, as well as to the use thereof for controlling such heat transfer systems.

BACKGROUND OF THE INVENTION

During evaporation and/or condensation, fluid in a heat transfer system is typically present in two phases, i.e. liquid and gas phase. The amount of fluid that is in the liquid phase and the amount of fluid that is in the gas phase can for example be expressed by the void fraction. The void fraction for a section of a tube in which the two-phase system exists is the ratio of the surface in the cross section that is in the gas phase to the total surface in the cross-section for the tube. For reasons of clarity, this is referred to as the cross-sectional void fraction. It is used as one of the key parameters for characterizing a two phase system.

Quite a number of experimental methods have already been proposed to measure the void fraction of a two phase system. Yet, most of these methods are either intrusive (disturb the liquid-gas flow), such as the conductive methods, not widely applicable (the optical methods) or very complex and expensive (e.g. gamma or neutron attenuation). Moreover, due to the physical limitations of many sensors mostly a volumetric (volume averaged) void fraction is determined.

In optical methods, visual images of the flow are processed to determine the void fraction. This requires a transparent tube (glass or plastic) which limits the possible temperatures and pressures. In International Journal of Heat and Mass Transfer, 48 (2005) 2970, Thome et al. developed an optical technique to determine the void fraction which showed a good agreement with the Rouhani-Axelsson drift flux void fraction model, described in Journal of Heat and Mass Transfer 13 (1970) 383. However, this optical method could only be used for stratified flow regimes, which limits the applicability of the measurement technique and can only be used when applying transparent tubes. Methods based on X-ray attenuation, do not require a transparent tube, yet there are serious cost and safety issues connected to this method.

Ultrasonic transmission techniques detect changes in acoustic impedance which is closely related to the density of the media. However, a gas-liquid interface acts almost as a perfect mirror for an acoustic wave. This technique can therefore only be used for total void fractions up to about 20%, which does not cover the full range of interest.

Capacitive void fraction measurements are often used, because they are quite easy to implement, non-intrusive and relatively low cost compared to some other techniques. A typical example for using capacitive measurements is based on measuring the volume averaged capacity between two curved electrodes mounted on the tube wall, the electrodes forming a capacitor. Nevertheless, due to the curvature of the electrodes, the measured capacitance is not only dependent on the void fraction but also on the spatial distribution of the phases. Hence, the measured capacitance does not vary linearly with the void fraction. In International Journal of Heat and Mass Transfer 53(2010) 5298, Canière et al. describes an example of the use of a capacitance sensor for characterizing a flow regime of a refrigerant based on the temporal and relative magnitude evolution of the capacitance of the capacitor. Nevertheless, the capacitive sensor used provides a signal related to the capacitance, but not to the actual void fraction value. Consequently, such methods do not allow void fraction measurement. In Flow Measurement and Instrumentation 10 (1999) 65, Keska et al. made a comparison of four techniques to measure the flow behaviour: a resistive method, a capacitive method, an optical method and a static pressure based method. It was concluded that the capacitive and resistive methods were both very effective to measure the flow behaviour.

In Journal of the Korean Nuclear Society 17 (1985) 1, Moon-Hyun et al. indicated that the relationship between the measured capacitance and the void fraction depends on the occurring flow regime. Moon-Hyun et al. disclosed steady (state) or stationary experiments in which the flow regime is known a priori because it is controlled in the experimental set-up. Dynamic or unsteady experiments were not discussed.

Therefore, there is still a need for an improved method and device for determining the void fraction of a multi-phase system, the method and device being usable in both steady as well as unsteady flow regimes.

An example of a system wherein a multi-phase system occurs is a refrigerator. In a refrigerator, the gas phase of a refrigerant tyically has a much lower density than the liquid phase. During evaporation, the flow will accelerate due to this density change, resulting in the occurrence of high velocities in the flow. Such high velocities cause a lot of friction and therefore pressure drop. To limit this pressure drop, the refrigerant flow is typically divided in several parallel circuits. At the inlet of the evaporator, a distributor with cappilary tubes divides the refrigerant over the several circuits. At the outlet, the different ciruits are connected to a collector, from which the refrigerant flows through a single tube again.

It is absolutely essential that the refrigerant at the outlet of the evaporator is fully evaporated and no liquid droplets remain in the flow. If liquid droplets would still be present, this would damage the compressor. Nevertheless, the heat transfer in each circuit can differ due to the variation of the position and amount of tubes. Typically, at the distributor, there is already two phase flow present. This two phase flow is distributed over the different parallel circuits in such a way that the refrigerant exits each ciruit in the same sligthly overheated state.

Due to the difference in heat flux for each circuit, attaining the same slightly overheated state for each circuit can only be obtained by proper design of the heat transfer system. Typically, in order to obtain a proper design, the cappilary tubes of the different circuits are selected to have different lenghts to obtain the proper conditions. Mostly, a trial and error method is used to determine the length of each cappilary tube. If the tube is too short, the mass flow rate of refrigerant in the circuit will be to high and the refrigerant will not be fully evaporated at the outlet. If the tube is too long, the mass flow rate will be to small and the refrigerant will be more overheated than necessary. The above method for designing is labour intensive and sub-optimal.

SUMMARY OF THE INVENTION

It is an object of embodiments of the present invention to provide good methods and systems for determining void fraction in channels.

It is an advantage of embodiments according to the present invention that capacitive measurements can be calibrated, thus allowing to determine the void fraction based on such measurements.

It is an advantage of embodiments according to the present invention that the void fraction can be determined for small channels and tubes.

It is an advantage of embodiments according to the present invention that the void fraction can be determined for multi-phase systems for which the difference between the dielectric constants of the phases is small such as for instance of refrigerants.

It is an advantage of embodiments according to the present invention that void fraction can be measured for complex channel geometries, such as for example for inclined tubes or bended tubes, and is not restricted to simple channel geometries, especially as such complex geometries may occur in real heat exchangers.

It is an advantage of embodiments according to the present invention that the void fraction is based on direct measurements and not determined indirectly by the use of models.

It is an advantage of embodiments according to the present invention that the systems and methods for determining void fraction are low cost.

It is an advantage of embodiments according to the present invention that the systems and methods for determining void fraction are non-intrusive to the multi-phase system.

It is an advantage of embodiments according to the present invention that systems and methods are provided that allow measurement of void fractions in the full range, i.e. from 0% void fraction to 100% void fraction and for all flow regimes.

It is an advantage of embodiments of the present invention that the systems and methods can be used for small diameter tubes, such as those typically used in heat exchangers.

It is an advantage of embodiments of the present invention that the method for void fraction determination is easy to use and does not require special safety measures.

It is an advantage of embodiments of the present invention that the sensor used for obtaining experimental data can be compact, while still allowing obtaining accurate results.

It is an advantage of embodiments of the present invention that a system and method is provided that allows determining the momentary or instantaneous void fraction of a multi-phase system.

It is an advantage of embodiments of the present invention that a system and method is provided that allows determining the cross-sectional void fraction of a multi-phase system.

It is an advantage of embodiments of the present invention that a system and method is provided that allows determining the void fraction of a steady as well as an unsteady multi-phase system.

It is an advantage of embodiments of the present invention that sufficiently fast sensing can be performed for sensing characteristic flow phenomena, so that the required information can be captured for accurately determining a void fraction.

It is an advantage of embodiments of the present invention that the methods and systems can be used in an operational phase as well as in a design phase.

The above objective is accomplished by a method and device according to the present invention.

The present invention relates to a method for determining the void fraction of a multi-phase system of at least one substance in a channel, the method comprising
measuring a void fraction dependent parameter of the multi-phase system,
obtaining a flow regime of the multi-phase system,
obtaining at least one multi-phase structure characteristic for the obtained flow regime,
obtaining a set of one or more relationships, specific for the obtained flow regime, between the void fraction dependent parameter and the void fraction, each of the relationships within one set corresponding to each of the obtained at least one multi-phase structures characteristic for the obtained flow regime
determining an occurring multi-phase structure,
determining the void fraction of the multi-phase system taking into account the relationship between the void fraction dependent parameter and the void fraction for the determined occurring multi-phase structure.

Obtaining at least one multi-phase structure characteristic for the obtained flow regime may be part of obtaining a flow regime of the multi-phase system. In other words, obtaining a flow regime of the multi-phase system may comprise obtaining at least one multi-phase structure characteristic for the obtained flow regime.

It is an advantage of embodiments according to the present invention that an accurate determination of the void fraction can be obtained. It is an advantage of embodiments according to the present invention that the method can be used for steady and unsteady flow regimes.

It is an advantage of embodiments according to the present invention that the method can be used to determine the cross sectional void fraction.

It is an advantage of embodiments according to the present invention that the method can be used to determine the instantaneous cross sectional void fraction.

Measuring a void fraction dependent parameter may comprise measuring an electric parameter. It is an advantage of embodiments according to the present invention that a non-destructive and a non-intrusive technique can be used for determining a void fraction.

Measuring a void fraction dependent parameter may comprise measuring an impedance of the multi-phase system. It is an advantage of embodiments according to the present invention that a relatively simple sensor can be used.

Determining the void fraction may comprise obtaining the set of one or more relationships to be used between the void fraction dependent parameter and the void fraction based on the obtained flow regime.

Obtaining the set of one or more relationships may be based on both the obtained flow regime and the obtained at least one multi-phase structure, whereby each of the relationships in the set corresponds to one of the characteristic, also referred to as typical, multi-phase structures occurring in the flow regime.

Obtaining the set of relationships may comprise retrieving the stored relationships specific for the occurring flow regimes and multi-phase structures.

Obtaining the set of relationships may comprise obtaining at least one non-linear relationship between the void fraction dependent parameter and the void fraction. Use of a non-linear relationship between the void fraction dependent parameter and the void fraction for the obtained flow regime assists in methods and systems providing a value for the void fraction with an improved accuracy.

Obtaining the set of one or more relationships between the void-fraction dependent parameter and the void fraction for a flow regime may comprise obtaining the characteristic, also referred to as typical, multi-phase structures, performing a numerical simulation, e.g. a finite element simulation, for deriving for the at least one multi-phase structure a relationship between an impedance, e.g. capacitance C, and an electromagnetic constant of a phase of the at least one substance of the multi-phase system, and for deriving, based thereon, a relationship between the impedance and the void fraction.

Measuring a void fraction dependent parameter may comprise measuring a void fraction dependent parameter in relative amplitude over time and wherein obtaining a flow regime of the multi-phase flow comprises determining the flow regime of the multi-phase flow based on the void fraction dependent parameter relative amplitude variation over time. It is an advantage of embodiments according to the present invention that the flow regime, the occurring multi-phase structure, as well as the void fraction itself can be based on measurement of a same parameter. In other words, it is an advantage of embodiments that no separate measurement technique needs to be provided for deriving a flow regime. Alternatively, a separate measurement technique may be used for obtaining the flow regime and or the occurring multi-phase structure in the channel.

Obtaining a flow regime of the multi-phase flow may comprise determining the flow regime of the multi-phase flow based on a flow map.

The present invention also relates to a system for determining the void fraction of a multi-phase system of at least one substance in a channel, the system comprising,
- a sensing unit for sensing a void fraction dependent parameter of the multi-phase system,
- a flow regime obtaining means for obtaining a flow regime of the multi-phase system
- a multi-phase structure obtaining means for obtaining a multi-phase structure of the obtained flow regime occurring in the multi-phase system
- a processor for determining the void fraction of the multi-phase system taking into account a relationships between the void fraction dependent parameter and the void fraction, the relationship being one out of a set of relationships being specific for the obtained flow regime and each of the relationships within one set corresponding to each of the at least one multi-phase structures characteristic for the obtained flow regime.

The sensing unit may comprise a capacitance sensor.

The sensing unit may have a length less than the inner diameter of the channel, wherein the length is measured in an axial direction of the channel.

It is an advantage of embodiments of the present invention that the cross-sectional void fraction can be determined. The system furthermore may comprise a memory storing a plurality of sets of relationships between the void fraction dependent parameter and the void fraction, each set of relationships corresponding with a predetermined flow regime.

The memory may store a non-linear relationship between the void fraction dependent parameter and the void fraction.

The memory may store a set of relationships between the void-fraction dependent parameter and the void fraction, the relationships taking into account an asymmetric multi-phase sectional distribution in the channel.

The flow regime obtaining means may comprise a processor for deriving a flow regime from a void fraction dependent parameter sensed over time.

The system may comprise a controller for performing a method as described above.

The present invention also relates to a controller for controlling a system for determining a void fraction, the controller being programmed for performing a method as described above.

The controller may be implemented as a computer program product for performing, when executed on a processing means, the steps of the method as described above.

The present invention also relate to a data carrier storing a computer program product being adapted for performing, when executed on a processing means, the steps of the method as described above.

The present invention also relates to the transmission of a computer program product over a wide or local area network, the computer program product being adapted for performing, when executed on a processing means, the steps of the method as described above.

It also is an object of the present invention to provide an efficient method for designing and/or controlling heat transfer systems, as well as to provide heat transfer systems thus obtained.

It is an advantage of embodiments of the present invention that a fast and structured method for designing a heat transfer system can be provided.

It is an advantage of embodiments of the present invention that for designing a heat transfer system use can be made of a fixed hardware setup of the heat transfer system, as designing can be performed by controlling a plurality of valves. In other words, the hardware construction itself does not need to vary for each heat transfer system to be designed, as according to embodiments of the present invention controlling a number of valves allows for providing the necessary design features. It is an advantage that the cost—both in time and economical—for designing a heat transfer system or a distributor thereof, can be reduced.

It is an advantage of embodiments of the present invention that the heat transfer system can also be controlled for optimal operation during use, i.e. after the design phase, to take into account effects of for example aging or changing environmental conditions.

The above objective is accomplished by a method and device according to the present invention.

The present invention relates to a heat transfer system, the system comprising a distributor, a plurality of parallel circuits of flow channels and a collector, the distributor arranged for distributing an incoming substance flow over a plurality of parallel circuits and the parallel circuits being combined in the collector for combining an output substance flow of each of the parallel circuits, wherein the heat transfer system comprises at least one valve for controlling the flow through a flow channel of at least one circuit, the at least one valve being controllable as function of a void fraction of a substance in the at least one circuit. The valve may be adapted for controlling the flow through a flow channel of one circuit. The at least one valve may be a valve for each of the circuits individually.

The heat transfer system may comprise at least one sensor in at least one of the plurality of circuits for sensing a void fraction dependent parameter of the substance flowing through the flow channel. The sensor may be a sensor used for sensing in one circuit. The sensor may be any type of sensor providing information of a void fraction of the substance flowing through the channel. The sensor may for example be based on X-ray, ultrasonic or optical imaging of the substance, may be based on measurement of a thermal parameter such as thermal conductance, may be based on an electromagnetic or electrical parameter such as for example an impedance, e.g. a capacitance, resistance, conductance, inductance . . . .

The heat transfer system may comprise a controller for controlling the at least one valve as function of a void fraction dependent parameter of the substance flowing through a flow channel of the circuit in which the flow is controlled by the at least one valve. The controller may operate according to a method described in any of the other aspects of the description of the present invention. The controller may comprise a flow regime obtaining means for obtaining a flow regime of the multi-phase system, and a processor for determining the void fraction of the multi-phase system taking into account a set of one or more relationships between the void fraction dependent parameter and the void fraction, the set of relationships being specific for the obtained flow regime. It is an advantage of embodiments according to the present invention that control of a heat transfer system to optimally operate the system can be performed in a substantially non-invasive manner, more particularly that the parameters required for control can be obtained in a non-invasive manner.

The controller typically may be connected to the at least one valve for controlling the at least one valve. It is an advantage of embodiments of the present invention that permanent control of the valve allows to adjust the heat transfer system to changing environmental conditions, changing temperature and/or changing phases in the system.

The controller may be adapted for controlling the at least one valve so as to induce a flow in the at least one circuit that only has an evaporated fraction of the substance in the circuit at the position where the at least one circuit is combined with other circuits. It is an advantage of embodiments according to the present invention that accurate operation of the system can be obtained, reducing the risk of damaging the heat transfer system.

The controller may be adapted for controlling the at least one valve so as to obtain an identical evaporation state in more or each of the parallel circuits. Alternatively, the controller may be adapted for controlling the at least one valve so as to obtain a variable evaporation state of more or each of the parallel circuits.

The controller may be adapted for controlling on/off operation of the heat transfer system, based on the obtained evaporation state for each of the parallel circuits.

The controller may form or be part of a control loop. The control loop may be a feedback control loop. The sensor also may be part of the feedback control loop.

The present invention also relates to a controller for controlling a heat transfer system, the controller being adapted for receiving, for at least one circuit in a set of parallel circuits in a heat transfer system, a void fraction dependent parameter of a substance flowing in the at least one circuit, and furthermore being adapted for controlling a valve in the at least one circuit for controlling the flow of the substance in the at least one circuit.

The controller may form or be part of a control loop. The control loop may be a feedback control loop.

The present invention furthermore relates to a method of designing and/or controlling a heat transfer system, the method comprising for at least one circuit of a set of parallel circuits of the heat transfer system, obtaining a void fraction dependent parameter of a substance flowing through the at least one circuit, and controlling a valve in at least on circuit of the set of parallel circuits so as to induce a flow in the at least one circuit that only has an evaporated fraction of the substance in the circuit at the position where the at least one circuit is combined with other parallel circuits, the controlling taking into account the obtained void fraction dependent parameter or a void fraction determined based thereon.

Alternatively or in addition thereto, the method may comprise controlling a valve in at least one circuit of a set of parallel circuits of the heat transfer system so as to obtain an identical evaporation state in more or each of the parallel circuits, the controlling taking into account the obtained void fraction dependent parameter or a void fraction determined based thereon. Alternatively, the method may comprise controlling a valve in at least one circuit of a set of parallel circuits of the heat transfer system so as to obtain a variable evaporation state of more or each of the parallel circuits, the controlling taking into account the obtained void fraction dependent parameter or a void fraction determined based thereon.

Obtaining a void fraction dependent parameter may comprise sensing a void fraction dependent parameter.

The method furthermore may comprise one, more or advantageously all of the method steps of the method for determining a void fraction described in any other aspect of the description of the present invention.

The method may be adapted for controlling operation of the heat transfer system based on the obtained evaporation state for one, more or advantageously all of the parallel circuits of the heat transfer system.

Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

Figure 1:
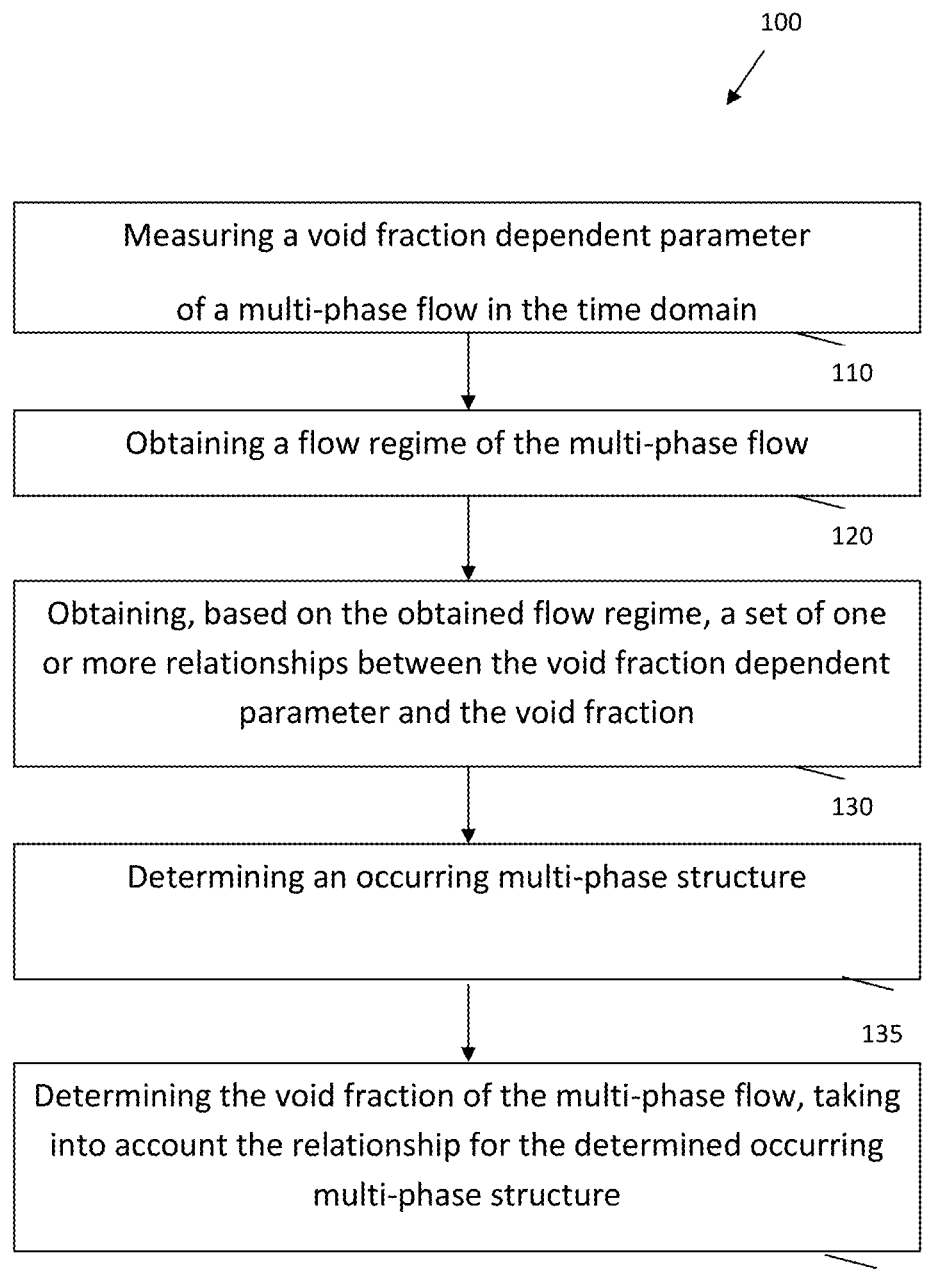
FIG. 1 illustrates an exemplary method for determining a void fraction according to an embodiment of the present invention.

The drawings are only schematic and are non-limiting. In the drawings, the size of some of the elements may be exaggerated and not drawn on scale for illustrative purposes.

Any reference signs in the claims shall not be construed as limiting the scope.

In the different drawings, the same reference signs refer to the same or analogous elements.

DETAILED DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

Where in embodiments of the present invention reference is made to mass flux G, it is meant the mass flow rate m divided by the cross sectional area of the channel A.

Where in embodiments of the present invention reference is made to vapour fraction x, it is meant the ratio of the vapour phase mass flow rate $m_v$ and the total mass flow rate m. Note that the vapour fraction is not equal to the void fraction if the phases have a different velocity, which is mostly the case.

Where in embodiments of the present invention reference is made a multi-phase system, reference is made to a system comprising two or more phases of a substance as well as to a system with more than one substance in the same phase or in different phases.

Where in embodiments of the present invention reference is made to void fraction of a multi-phase system, reference may be made to the fraction of one phase or substance of the multi-phase system in a section. Such a fraction of one phase may for example be a fraction of a gaseous or vapour phase compared to the section of the channel. In that respect a difference should be made between the cross-sectional void fraction, ideally this is an infinitely small cross section, in practice it means the void fraction in a section with length equal to or smaller than the diameter of the channel, and the volume void fraction, this is a volume averaged void fraction of a section with a length larger than the diameter of the channel. Where in embodiments of the present invention reference is made to void fraction, reference may be made to the cross-sectional void fraction. Where in embodiments of the present invention reference is made to a steady flow regime system or steady multi-phase system, reference is made to a system in which the flow regime does not change over time and where the one flow regime comprises one multi-phase structure of which the geometrical parameters may or may not change over time.

Where in embodiments of the present invention reference is made to a unsteady flow regime system or unsteady multi-phase system, reference is made to a system in which the flow regime may or may not change over time and where, one or more of the occurring flow regimes comprises more than one multi-phase structure which change over time and where the geometrical parameters of one or more of the multi-phase structures may or may not change over time.

In one aspect, the present invention relates to a method for determining the void fraction of a multi-phase system of one or more substances in a channel. It thereby is advantageous that the method can be non-intrusive and that it can be applied to different shapes and geometries of channels, such as for example to curved channels. According to embodiments of the present invention, the method comprises measuring a void fraction dependent parameter of the multi-phase system. Advantageously the void fraction dependent parameter may be an electromagnetic parameter, advantageously being an electrical parameter such as an impedance more explicitly a capacitance measured over or in the channel wherein the substance flows or over or in part of the channel. Other void fraction dependent parameters and signals can be derived from optical inspection, density differences, ultrasonic measurements or x-ray measurements. According to embodiments of the present invention, the method also comprises obtaining a flow regime of the multi-phase system. The latter may advantageously be obtained based on the measured void fraction dependent parameter of the multi-phase flow.

The method, according to embodiments of the present invention, also comprises determining the void fraction of the multi-phase system taking into account a relationship between the void fraction dependent parameter and the void fraction, the relationship being specific for the occurring multi-phase structure. The occurring multi-phase structure may be a momentary or instantaneous occurring multi-phase structure, i.e. a multi-phase structure occurring at a specific moment in time. The occurring multi-phase structure may also be a multi-phase structure occurring during a certain time interval, the time interval preferably being smaller than the time interval between consecutive multi-phase structures typically occurring in the obtained flow regime. The occurring multi-phase structure is one of the set of multi-phase structures typically occurring in the obtained flow regime. It has been found that accurate determination of the void fraction thus can be obtained, whereby the obtained values effectively express a void fraction, and not a parameter related thereto. It has been found that this method allows to determine the void fraction both for steady and unsteady regime. It has been found that this method allows to determine the cross-sectional void fraction.

The multi-phase flow does not need to be limited to a combination of a liquid phase and a vapour or gaseous phase. The multi-phase flow may for example also be a combination of oil and water, a combination of different liquids, a combination of different solids, a combination of liquids and solids, a liquid system contaminated with fouling, a slurry i.e. a fluid mixture of a pulverized solid with a liquid etc. The void fraction can then be regarded as the relative percentage of the volume of one of the phases, with respect to the total volume of the phases. Examples of such multi-phase flow systems are evaporating or condensing refrigerants, ice slurries, . . . .

By way of illustration, embodiments of the present invention not being limited thereto, the method will further be described with reference to FIG. 1 illustrating an exemplary method for void fraction determination comprising standard and optional steps of methods according to embodiments of the present invention.

Figure 2:
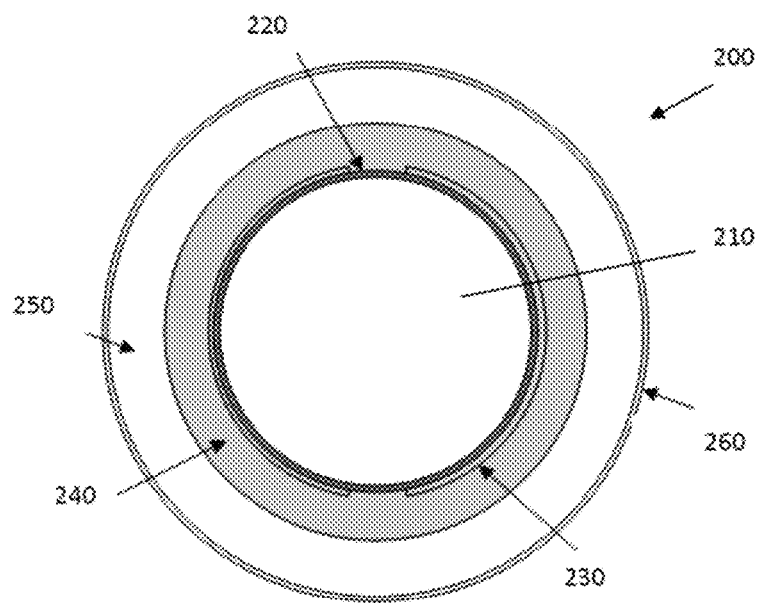
FIG. 2 illustrates a cross-section of an example of a capacitive sensor as can be used in methods and systems for determining a void fraction according to an embodiment of the present invention.

The method 100 for determining a void fraction of a multi-phase system comprises in one step 110 measuring of a void fraction dependent parameter of a multi-phase system. In one particular set of embodiments, measuring a void fraction dependent parameter comprises measuring a capacitance over or in a channel wherein the multi-phase system occurs. Measuring may be performed with a predetermined measurement setup such as for example the sensor configuration as shown in FIG. 2. Measuring a capacitance may be performed using a set of curved capacitor plates, e.g. when measuring in tube shaped channels, the multi-phase system in the channel being the dielectric medium of the capacitor.

In another step 120, the present invention also comprises obtaining a flow regime of the multi-phase system. The flow regime is a classification of multi-phase systems according to the characteristically occurring multi-phase structures, the characteristic sequence in which these multi-phase structures occur in time and the characteristic variations in time and amplitude of the geometrical parameters of these multi-phase structures. A multi-phase structure is a spatial distribution of the phases of a multi-phase system at one moment in time in the cross section of a channel. As an illustration, embodiments of the present invention not being limited thereto, examples of a multi-phase structure in a circular channel can be a circular liquid ring with a gas core at the center as shown in FIG. 13*a* and a stratified liquid layer at the bottom of the tube with a gas layer on top as shown in FIG. 10*b*. For one type of multi-phase structure, the geometrical parameters of the spatial distribution can vary, for example if the multi-phase structure type is a circular liquid ring with a central gas core, the thickness of the ring can vary.

Hence, obtaining a flow regime corresponds to obtaining the characteristic time sequence of the characteristic multi-phase structures and/or their geometrical parameters. Obtaining a flow regime may comprise obtaining at least one multi-phase structure characteristic for the obtained flow regime.

Obtaining the flow regime in one embodiment may be performed through an input port, where information regarding the flow regime, e.g. determined using another device not being part of the system according to an embodiment of the present invention, is obtained as data input. Alternatively thereto, the flow regime also may be determined. The latter can be performed in a plurality of ways. In one advantageous embodiment, determining the flow regime may be based on the measured void fraction dependent parameter of the multi-phase system in step 110. In a particular example the void fraction dependent parameter is measured over time. Based on the obtained results, the flow regime can be determined. More particularly, based on a set of reference values obtained during test measurements at varying mass flux G and vapour fraction x, a flow regime can be discriminated by comparing the relative magnitude evolution over time of the void fraction dependent parameter with the obtained reference values and deriving based thereon a flow regime. The reference data can be obtained in a plurality of ways, e.g. using a probabilistic unsupervised flow mapping technique, using a large variety of measurements and setting up a look up table, using predetermined algorithms, etc. In at least some embodiments, the statistical and frequency parameters of the sensor signal can thus be used for determining the flow regime. In another example, use is made of a flow map to obtain the flow regime. Several flow maps are available in literature, yet one should note that most flow maps are only valid for a certain range of refrigerants, geometries and conditions. For example, for horizontal two phase flows of common refrigerants in small diameter tubes, the Wojtan-Ursenbacher-Thome flow map as described in International Journal of Heat and Mass transfer 48 (2005) 2955-2969 could be used. The number of flow regimes that are considered in the method, may be selected as appropriate. It is possible to determine the number of flow regimes required for the application based on the measurements of the void fraction dependent parameter. This includes assuming an appropriate number of flow regimes and evaluating the quality of distinction between the resulting determined flow regimes. In case this quality is too low the appropriate number of flow regimes to be selected is less than the assumed number. The quality of distinction may be determined based on a number of statistical parameters obtained based on the sensor signals that were determined.

Once the flow regime has been determined, the characteristic set of one or more multi-phase structures and the order in which they occur in time has been determined. This means that from the void fraction dependent parameter it can be derived which multi-phase structure instantaneous appears. For each of these multi-phase structures the relationship to be used between the void fraction dependent parameter and the void fraction can be obtained. The void fraction is directly linked to the geometrical parameters of the multi-phase structure. The latter is indicated in step 130 of the flow chart of FIG. 1. Hence, typically, per flow regime a set of one or more relationships between the void fraction dependent parameter and the void fraction may be stored, each of the relationships within one set corresponding with a characteristic multi-phase structure of a particular flow regime, the number of sets being equal to the number of different flow regimes. The number of relationships depends on the type of flow regimes and whereby steady flow regimes are characterized by a single relationship only because such flow regimes consist of only one multi-phase structure, whereby unsteady flow regimes are characterized by a set of relationships. Obtaining then may correspond with retrieving the relationship corresponding with the flow regime obtained in step 120. The stored relationships may be previously determined. By way of illustration, embodiments of the present invention not being limited thereto, an example of how a relationship can be derived will be further discussed in the example provided below. In some embodiments, the relationship may be established by determining, for the flow regime, and for each multi-phase structure of the multi-phase system in the channel and then performing a numerical simulation such as for example a finite element simulation, a finite volume simulation, a finite differences simulation or a boundary element method simulation, for deriving a relationship between a capacitance C and a dielectric constant of the flowing substance, and for deriving, based thereon, a relationship between a capacitance C and the void fraction.

Obtaining a relationship may also comprise determining the relationship. Determining the relationship may comprise calculating the relationship based on finite element simulations.

The method according to the present invention further comprises the step 135 of determining an occurring multi-phase structure at a certain time or time interval.

The method according to the present invention may further comprise the step of determining the temperature and/or pressure of the substance in the channel. Obtaining a relationship between the void fraction dependent parameter and the void fraction may then comprise obtaining the relationship corresponding with the determined temperature and/or pressure.

In case the void fraction dependent parameter is for instance a capacitance C, obtaining a relationship between the void fraction dependent parameter and the void fraction may comprise selecting the dielectric constant corresponding with the determined temperature and/or pressure. For the latter case, the dielectric constant in function of the temperature may be stored. If this is not the case, the dielectric constant can also be determined with additional measurements. For each of the phases a measurement has to be performed wherein this phase is taking in the full cross section of the channel. Hence the number of additional measurements needed is equal to the number of phases.

The method according to the present invention may further comprise selecting substance properties, such as for instance the dielectric constant, corresponding with the determined temperature and/or pressure, and using said selected substance property in determining the void fraction dependent parameter and the relationship between the void fraction dependent parameter and the void fraction. It is an advantage of the embodiments of the present invention that these properties can be determined (relative to a reference). It is an advantage that the curves can be determined using properties determined with the system according to the present invention instead of having to rely on tabulated values, which are often hard to come by for a wide range of refrigerants and environmental conditions. The latter would limit the flexibility of the method. Determining the properties with the system according to the present invention hence allows for a broad applicability of the present invention.

The relationships that are stored or one or more thereof may be nonlinear relationships between the void fraction dependent parameter and the void fraction. The relationships or one or more thereof may take into account an asymmetric liquid-vapour multi-phase structure in the channel. The relationships or one or more thereof may take into account the multi-phase structure(s). The channel may have any orientation such as upright or horizontal position.

In a further step 140, the void fraction of the multi-phase system is determined, taking into account the set of relationships between the void fraction dependent parameter and the void fraction corresponding with the determined occurring multi-phase structure. This may for example be performed by taking the measured void fraction dependent parameter or part thereof and by using the relationship, out of the set of relationships, corresponding to the occurring multi-phase structure for determining the corresponding void fraction. The corresponding result, i.e. the determined void fraction, may be outputted to the user, or it may be directly used as data for determining a parameter regarding the process wherein the flow occurs, e.g. for determining a performance or status of a cooling or heating process.

Other standard and optional steps, known by the person skilled in the art, also may be present in the method. Further features and advantages may for example correspond with one or more features and advantages of the example with experimental results described below.

According to embodiments of the present invention, the method may be implemented as a computer-implemented invention or a computer or controller driven method, allowing a high degree of automation.

Embodiments according to the present invention may be implemented for designing systems such as heat and/or cooling systems and thus be used during a design phase. Alternatively or in addition thereto, the methods also may be implemented for controlling systems such as heat and/or cooling systems and thus be used during use of such systems.

In another aspect, the present invention relates to a system for determining the void fraction of a multi-phase system of a substance in a channel. The system can for example be positioned in or near an existing cooling and/or heating system for checking of the operation or controlling of the operation during use. Alternatively the system also can be used for designing cooling and/or heating systems.

According to embodiments of the present invention, the system comprises a sensing unit for sensing a void fraction dependent parameter of the multi-phase system, a flow regime obtaining means for obtaining a flow regime of the multi-phase system of the substance, and a processor for determining the void fraction of the multi-phase system taking into account the set of relationships between the void fraction dependent parameter and the void fraction, the relationships being specific for the obtained flow regime.

Figure 3:
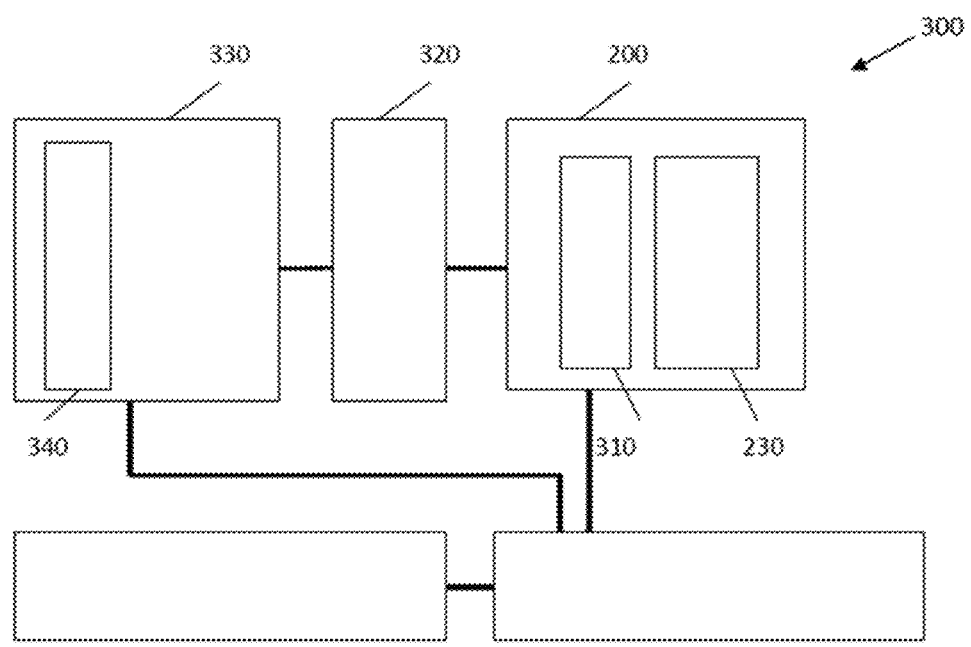
FIG. 3 illustrates a schematic overview of standard and optional components of a system for determining a void fraction according to an embodiment of the present invention.

By way of illustration, further features and advantages of embodiments of the present invention will be described with reference to FIG. 2 and FIG. 3, FIG. 2 illustrating a particular design of a sensing unit 200 implemented in a channel and FIG. 3 illustrating an overall schematic representation of a system 300 according to an embodiment of the present invention. In FIG. 2 a sensing unit as can be used in a system 300 according to an embodiment of the present invention is shown. The sensing unit thereby is implemented in a channel 210. In the present example, the channel is a tube having a tube wall 220, to which electrodes 230 are applied. In the example shown, the sensing unit 200 corresponds with a capacitance sensor. The tube of the present example furthermore comprises a PVC surrounding 240, an epoxy surrounding 250 and an inox casing 260. It will be clear that the exact shape and components of the tube or channel will have an effect on the outcome of the measurements, but will not limit the method or system from being used except that the cross-sectional accuracy should be high enough to detect different multi-phase structures occurring alternately in time. The bandwidth of the sensor therefore may be higher than the (highest) frequency of the occurring characteristic flow phenomena. The latter may be accomplished with a sensor of length less than the inner diameter of the channel or tube in which the multi-phase system occurs. If that is the case, one can state that the sensor allows the determination of parameters linked to the cross sectional void fraction instead of to the volume averaged void fraction. In other words, the system and method according to embodiments of the present invention are applicable to any type of channel wherein the multi-phase system occurs. Furthermore, the basic components of the measurement unit, in the present example being the electrodes, do not need to be implemented in the channel. These also may be separate. The electrodes, through which the signals are measured, advantageously are positioned close to the part where the flow occurs. In some advantageous embodiments, use is made of shaped electrodes that can closely fit to the wall of the channel wherein the flow occurs. Such shaped electrodes may e.g. be curved electrodes. An example of such a sensing unit is for instance described Canière et al, Experimental Thermal and Fluid Science, 32 (2008) 892-904, which is incorporated herein as reference. In this case the length of the sensor electrodes is exactly one inner tube diameter.

In FIG. 3 an overview is given of different standard and optional components of the system. The system 300 comprises a sensing unit 200, implemented in the channel wherein the flow occurs or not. In the latter case, during application the sensing unit 200 typically is positioned close to the channel wherein the flow occurs. The sensing unit 200 typically may comprise sensing elements 230 connected to a signal generating and/or processing component 310. If for example a capacitance sensing unit is used, the sensing elements (230), i.e. electrodes, are combined with a number of electrical components (corresponding with the signal generating and/or processing component 310) allowing to derive a capacitance measurement. In some embodiments, the sensor is equipped with high precision fast switching circuits. The components may be selected such that a required resolution can be obtained, which in some examples may be as low as 5 fF or lower.

According to embodiments of the present invention, the system furthermore comprises a flow regime obtaining means 320 for obtaining information regarding the flow regime. The latter may be an input port for receiving such information, or it may be a processing means for determining the flow regime. In advantageous embodiments, the processing means may be adapted for determining the flow regime based on measurements performed with the sensing unit. Alternatively or in addition thereto, other information may be used for deriving the flow regime. The processing means may be programmed to have the functionality as described in step 120 of the method 100 as described above.

According to embodiments of the present invention, the system furthermore comprises a multi-phase structure obtaining means for obtaining a multi-phase structure of the obtained flow regime occurring in the multi-phase system at a certain moment in time or during a certain time interval. Obtaining a multi-phase structure may or may not comprise determining the multi-phase structure. The multi-phase obtaining means may be an input port for receiving such information, or it may be a processing means for determining the multi-phase structure. In advantageous embodiments, the processing means may be adapted for determining the occurring multi-phase structure based on measurements performed with the sensing unit. The processing means may be programmed to have this functionality.

Further according to embodiments of the present invention, a processor 330 may be provided for determining the void fraction of the multi-phase system taking into account a (set of) relationship(s) between the void fraction dependent parameter and the void fraction, the (set of) relationship(s) being specific for the obtained flow regime. Such a processor may comprise a relationship selecting means for selecting the relationship between the void fraction dependent parameter and the void fraction that corresponds with the multi-phase structures of the determined flow regime, i.e. each multi-phase structure has one relationship between the void fraction and the void fraction dependent parameter. Such a processor may comprise a relationship selecting means for selecting the relationship between the void fraction dependent parameter and the void fraction that corresponds with the obtained occurring multi-phase structure occurring at a certain moment in time or during a certain time interval, obtained in a previous step.

The system according to embodiments of the present invention furthermore may comprise a memory 350 storing a plurality of (set of) relationships between the void fraction dependent parameter and the void fraction, each set corresponding with a predetermined flow regime. Such a memory 350 may be any suitable type of memory. The memory may store at least one non-linear relationship between the void fraction dependent parameter and the void fraction corresponding with the multi-phase structure of a particular flow regime. It furthermore or alternatively may store at least one relationship between the void-fraction dependent parameter and the void fraction, wherein each relationship takes into account a multi-phase structure with an asymmetric multi-phase spatial distribution in the cross section of the channel for the corresponding flow regime. It furthermore or alternatively may store at least one relationship between the void-fraction dependent parameter and the void fraction, the relationship taking into account the flow regime.

The system 300 also may comprise a controller 360 for controlling the different components of the system. The controller may be adapted for performing control of the different components in such a manner that a method as described above is performed.

In one aspect, the present invention also relates to a controller for controlling a system for determining a void fraction. The controller thereby may be programmed for performing the method as described in embodiments of the first aspect. Such a controller may be implemented in hardware as well as in software.

In one aspect, the present invention also relates to a controller of the void fraction in a system such as a heating or cooling device.

In other words, the present invention in one aspect also relates to a computer program product which provides the functionality of any of the methods according to the present invention when executed on a computing device. Such computer program product can be tangibly embodied in a carrier medium carrying machine-readable code for execution by a programmable processor. The present invention thus relates to a carrier medium carrying a computer program product that, when executed on computing means, provides instructions for executing any of the methods as described above. The term "carrier medium" refers to any medium that participates in providing instructions to a processor for execution. Such a medium may take many forms, including but not limited to, non-volatile media, and transmission media. Nonvolatile media includes, for example, optical or magnetic disks, such as a storage device which is part of mass storage. Common forms of computer readable media include, a CD-ROM, a DVD, a flexible disk or floppy disk, a memory key, a tape, a memory chip or cartridge or any other medium from which a computer can read. Various forms of computer readable media may be involved in carrying one or more sequences of one or more instructions to a processor for execution. The computer program product can also be transmitted via a carrier wave in a network, such as a LAN, a WAN or the Internet. Transmission media can take the form of acoustic or light waves, such as those generated during radio wave and infrared data communications. Transmission media include coaxial cables, copper wire and fibre optics, including the wires that comprise a bus within a computer.

Alternatively or in addition thereto, a processor or controller according to an aspect or embodiment of the present invention may be implemented in hardware.

Such a controller or processor may be a processing system that includes at least one programmable processor. Such a processor may be coupled to a memory subsystem that includes at least one form of memory, e.g., RAM, ROM, and so forth. It is to be noted that the processor or processors may be a general purpose, or a special purpose processor. Thus, one or more aspects of the present invention can be implemented in digital electronic circuitry, or in computer hardware, firmware, software, or in combinations of them. The processing system may include a storage subsystem that has at least one disk drive and/or CD-ROM drive and/or DVD drive. In some implementations, a display system, a keyboard, and a pointing device may be included as part of a user interface subsystem to provide for a user to manually input information. Ports for inputting and outputting data also may be included. More elements such as network connections, interfaces to various devices, and so forth, may be included. The various elements of the processing system may be coupled in various ways, including via a bus subsystem. The memory of the memory subsystem may at some time hold part or all of a set of instructions that when executed on the processing system implement the steps of the method embodiments described herein.

By way of illustration, embodiments of the present invention not being limited thereto, a number of experimental results are discussed below, illustrating features and advantages of some embodiments of the present invention.

First the experimental conditions are described under which experimental results are obtained. A method according to an embodiment of the present invention is performed using 270 measurement points. For all these measurement points, the tube used was a straight round tube having a tube diameter D of 8 mm. The mass flux ranged from 200 to 500 kg/m$^2$s and the vapour fraction ranged between 2.5% to 97.5%. For the examples, refrigerants R134a and R410A were used. The results were compared to the Rouhani-Axelsson drift flux void fraction model, which in prior art typically is considered to be a good model.

The sensor used consisted of two concave electrodes, both with an angle of 160° and a length of 8 mm. Flexible circuit material (R/Flex® 3000 from Rogers Corporations) was used to form the tube wall in the sensor, whereby the electrodes were etched out of the copper cladding on this circuit material. The thickness of the dielectric layer was 50 μm±12.5%, it had an electrical resistance of $10^{12}$ MΩ/cm and its dielectric constant was 2.9 at 23° C. After etching the electrodes on the circuit material, it was glued in PVC parts, which provided the structural strength. These PVC parts were then placed into a stainless steel cylindrical casing, and the annular gap between the PVC and the casing were filled with an epoxy resin. By way of illustration, embodiments of the present invention not being limited thereby, a cross section of the capacitive sensor as used in the present example is shown in FIG. 2. The sensor furthermore was equipped with high precision fast switching circuits so that the required resolution could be obtained. In one example, the resolution that could be obtained was smaller than 5 fF.

Figure 4:
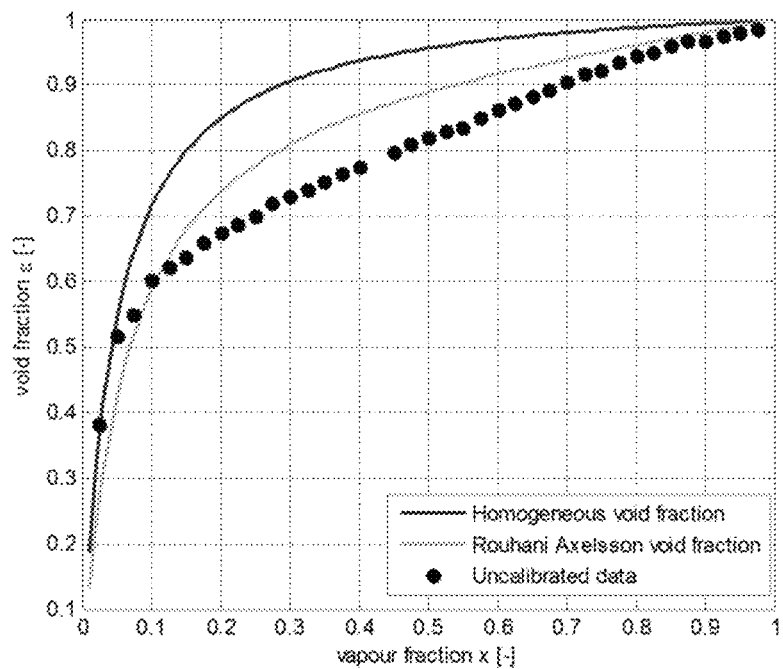
FIG. 4 illustrates void fractions measured for a sensor wherein the dependency on the flow-regime is considered linear, compared to predicted results based on the Rouhani-Axelsson drift flux void fraction model and the homogeneous void fraction model, illustrating the need for embodiments according to the present invention.

First, by way of illustration, it is shown that using a linear relationship for the dependency of the capacity as function of the void fraction for an example of R410A as refrigerant, T=15° C., G=200 kg/m$^2$s and D=8 mm, does not render a good agreement with the existing models. The experimental results (referred to as 'uncalibrated data') obtained are compared with the void fraction predicted by the Rouhani-Axelsson drift flux void fraction model and with the homogeneous void fraction model, as shown in FIG. 4. One can see that the measured values do not agree with the Rouhani-Axelsson drift flux void fraction model, which was shown to be one of the most accurate void fraction models for this kind of flow.

In the present example, use is made of a calibrated sensor for determining void fraction according to an embodiment of the present invention. First it will be illustrated how calibration is performed in the present example. Thereafter the obtained results will be discussed in more detail.

By calibrating, the relationships between the measured capacity C and the void fraction for this sensor which are dependent on the multi-phase spatial distribution in the cross section of the channel between the electrodes is taken into account. Each relationship hence corresponding to a C-ε curve differs according to the multi-phase structure, and each set of relationships differs according to the flow regime. Hence, in the present example several calibration curves were determined, one for each multi-phase flow structure that occurs in the different flow regimes, so that these calibration curves could be taken into account, in agreement with an embodiment of the present invention. For obtaining appropriate results, the experimental results were obtained using also automatic flow regime detection. To determine these calibration curves, in the present example, a set of some simplified gas-liquid multi-phase structures were assumed for each flow regime. In the present example, the multi-phase structures used were selected to incorporate the effect of the flow regime on local heat transfer and pressure drop, allowing to also accurately predict the local heat transfer and pressure drop, compared to e.g. correlations that do not incorporate this information. Finite Element Method (FEM) simulations were used to determine the C-ε relation for each of these liquid-vapour multi-phase structures. FEM simulations were preferred to determine the calibration curves because they allowed to precisely determine the sensor output for relatively complex liquid-vapour multi-phase structures. If inserts would be used to mimic the vapour and liquid phase multi-phase structure in the channel, this would considerably limit the shapes and dimensions that can be tested. Moreover, these inserts would need to have the same dielectric constant as the phases, or at least a similar dielectric constant. Nevertheless, in certain embodiments of the present invention, the use of inserts is not to be excluded.

Figure 5:
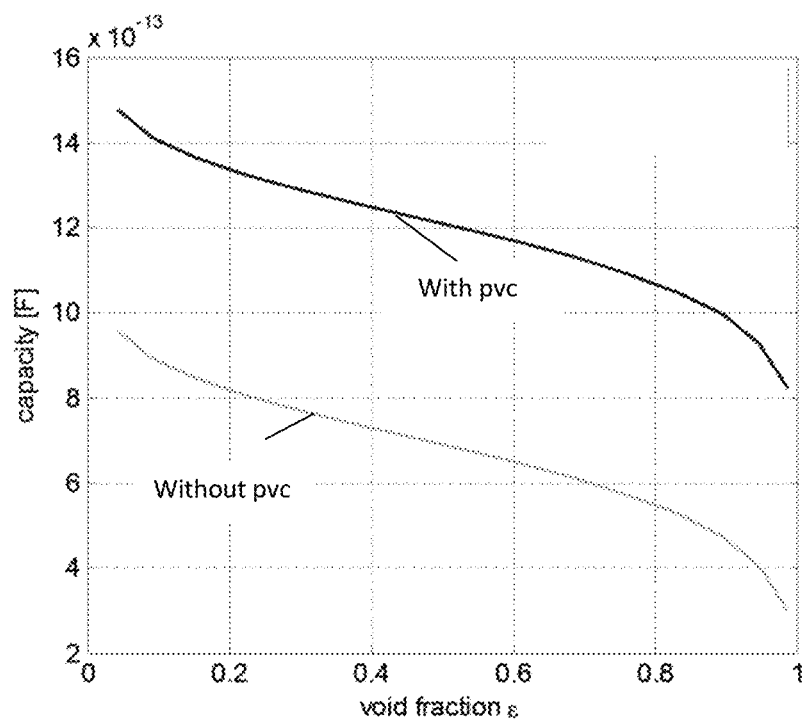
FIG. 5 illustrates a FEM simulation of measured capacity for a sensor with and without PVC surrounding, illustrating the effects of sensor design that can be taken into account in an embodiment of the present invention.

Determining the Dielectric Constant:

The dielectric constant $\varepsilon_r$ of both phases of the refrigerant was determined. In the literature for R134a $\varepsilon_{liq}$=9.51, $\varepsilon_{vap}$=1.0125 and for R410A $\varepsilon_{liq}$=7.78, $\varepsilon_{vap}$=1.0078 was found (both at ambient temperature). For a single phase system, the measured capacity is directly proportional to the dielectric constant of the fluid. For a two phase system, the dielectric constant of both phases also strongly influences the measured capacity, hence the dielectric constant needs to be determined as accurate as possible. Therefore, the dielectric constant of both phases is derived from actual measurements of the capacitive sensor rather than by using an estimation method. For each refrigerant a measurement for x=0 and for x=1 was taken, both at 15° C. The electronic transducer measured the capacitance between the electrodes at 2 MHz, this design was based on the charge-discharge principle. The electric current that exists due to this charging and discharging is converted to a voltage signal. The voltage signal is measured at a sample frequency of 1 kHz by a DAQ system. The transducer gain is 1.16V/pF, the uncertainty evaluated as 2σ is ±4 mV. Based on this measurement, the dielectric constant cannot be derived directly because the measured capacity is not only due to substances in between the electrodes, but also includes contributions due to the construction of the sensor. Due to fringing effects of the electrical field lines, the PVC, epoxy and stainless steel casing surrounding the electrodes, result in an offset capacity on top of the capacity of the two phase system. This is illustrated with a simplified FEM simulation considering the electrodes surrounded by only PVC. For this FEM simulation, the flow was assumed to be stratified, varying the stratified liquid layer height results in a varying void fraction. The following settings were used: $\varepsilon_{liquid}$=8.3, $\varepsilon_{vapour}$=1.5, $\varepsilon_{PVC}$=4 and the outer diameter of the PVC part surrounding the sensor plates is 30 mm. The result of this simulation is shown in FIG. 5, where it is compared to a simulation for the same conditions without PVC surrounding the plates. It can be clearly seen that the capacity with PVC is higher than the one without, and that the difference is independent of the void fraction, it is an 'offset'. By measuring the capacity for x=1 and x=0, the difference in the measured capacity for liquid and gas $\Delta C_{LV}$ is known and because the offset is independent of the void fraction $\Delta C_{LV}$ is independent of the offset. For R134a this difference was found to be 1.185±0.0049 pF and for R410A this difference was 1.177 pF±0.0049 pF. If the dielectric constant of one of the phases is known, the dielectric constant of the other phase can be derived from $\Delta C_{LV}$. For a gas, the dielectric constant is typically small, mostly just larger than 1. Hence, if the dielectric constant of the vapour phase can be estimated to be e.g. 1.5, the capacity for vapour $C_{vap}$ can be found using 3D FEM simulations. If $\Delta C_{LV}$ is known, the capacity for liquid can be calculated as $C_{liq}=C_{vap}+\Delta C_{LV}$. Finally, from $C_{liq}$ the dielectric constant of the liquid $\varepsilon_{liq}$ can be derived using 3D FEM simulations.

Figure 6:
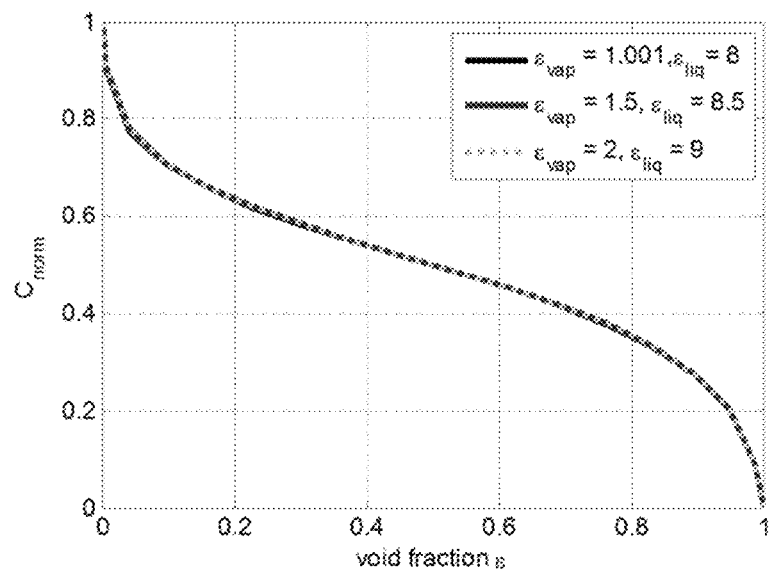
FIG. 6 illustrates that the effect of the estimate used for determining the dielectric constant is limited for a predetermined algorithm for determining the dielectric constant, as can be used in embodiments according to the present invention.

It is important to remark here that the value found for $\varepsilon_{liq}$ is dependent on the estimate of $\varepsilon_{vap}$. The absolute value of $\varepsilon_{vap}$ is not known, only that it is close to 1. Hence some FEM simulations were performed to estimate the effect of an incorrect value of $\varepsilon_{vap}$ on the calibration curves. In FIG. 6 the results of these FEM simulations are shown. The flow regime is stratified for which a typical multi-phase structure occurring in this flow regime has been chosen and three different cases of $\varepsilon_{vap}$ are simulated, for all these simulations $\Delta C_{LV}$=1.28 pF. In this Figure, the normalized C-ε relation is shown for each case, $C_{norm}$ is determined as follows:

$$C_{norm} = \frac{C_{measured} - C_{vapour}}{C_{liquid} - C_{vapour}} \qquad (1)$$

It can be seen that the difference between the curves is minimal. For other multi-phase structures the conclusion was the same; these figures are not shown here for sake of simplicity. FIG. 6 thus shows that, if the difference between the actual and the estimated $\varepsilon_{vap}$ is relatively small, the normalized calibration curves will not be affected if $\Delta C_{LV}$ is known. In conclusion, the dielectric constant of the phases used to determine the calibration curves in the following section are found as follows. In a first step, the dielectric constant for the vapour phase is assumed to be in the range 1.5-2. In a second step, $C_{vap}$ is calculated for the given sensor geometry. In a third step, $C_{liq}$ is calculated as $C_{vap}$ $\Delta C_{LV}$. In a fourth step, $\varepsilon_{liq}$ is derived from FEM simulations for a void fraction of 0. As such, $\varepsilon_{liq}$ was found to be 8.19 for R410A and 8.25 for R134a. These values are comparable with data from open literature, and are used for all further FEM simulations except when it is otherwise specified.

Determination of the Flow Regime:

In order to calibrate the capacitive sensor taking into account the distribution of the phases in the cross section of the channel, the multi-phase spatial distributions that are possible need to be known. The possible (typical, characteristic) distributions depend on the flow regime and can also be very unsteady such as for an intermittent or slug flow, whereby large scale structures pass through the electrodes. Based on a large set of test measurements at varying mass flux and quality, a flow regime discriminator could be obtained, allowing to identify, based on the capacitance values recorded in a particular case, what the flow regime is. Whereas in the current example, the flow regime discriminator was based on a probabilistic unsupervised flow mapping technique, whereby a flow regime was assigned to each point of a recorded dataset, embodiments of the present invention are not limited thereto, and other ways of establishing a flow regime discriminator also could be used. In the current example, a three group classification was considered: slug, annular and intermittent flow.

Figure 7:
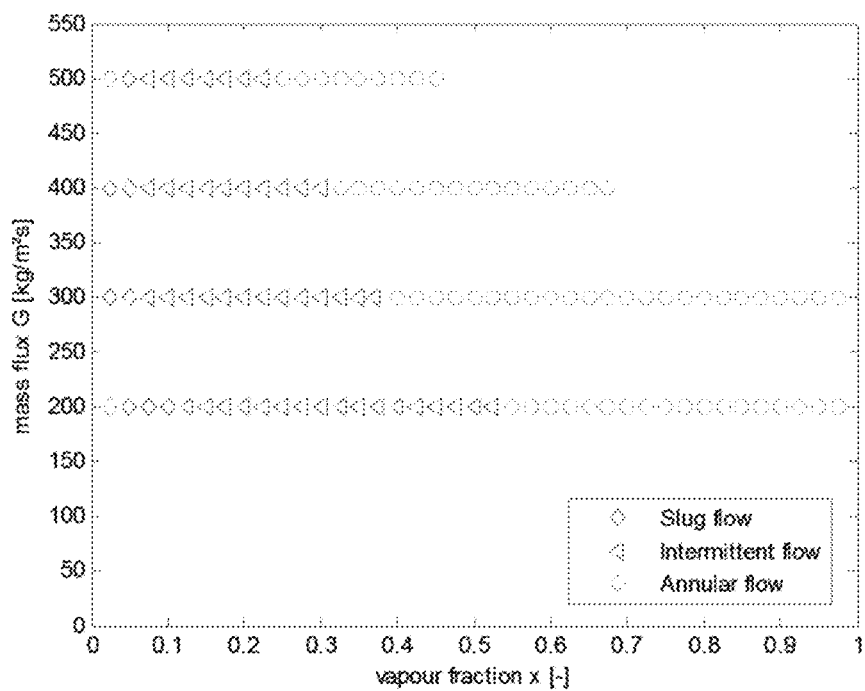
FIG. 7 and FIG. 8 illustrate the results of a flow mapping technique for refrigerants R134a and R410A respectively, as can be used in embodiments according to the present invention.
Figure 8:
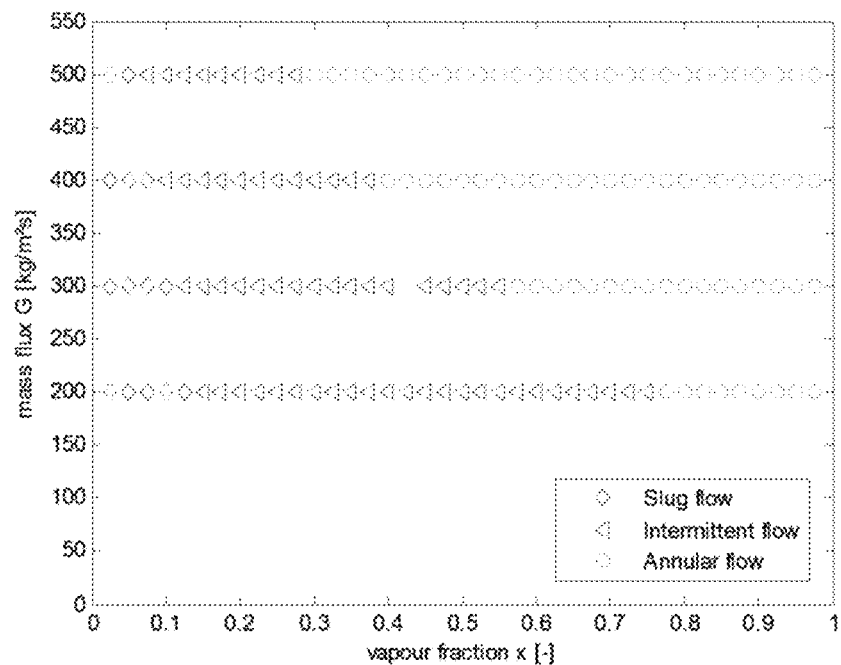

Each of these flow regimes can be characterised by characteristic time sequences of characteristic liquid-vapour multi-phase structures. For flow regimes like slug or stratified wavy flows, characteristic multi-phase structures are characterised in the sense that the liquid will be located mainly at the bottom of the tube. For annular flow, multi-phase structures tend to be characterised by the liquid forming a ring shaped film on the inner wall of the tube, which can be thicker at the bottom. The resulting flow regime classification as a function of the vapour fraction and mass flux used in the present example is shown in FIG. 7 and FIG. 8. For these results, the selected temperature was 15° C. and the diameter was 8 mm. The results also showed that the probabilistic approach reveals the actual flow physics in an accurate manner. In the next section the assumed set of multi-phase structures for each flow regime are discussed.

Flow Regimes Used in the Present Example

Slug Flow

Figure 9:
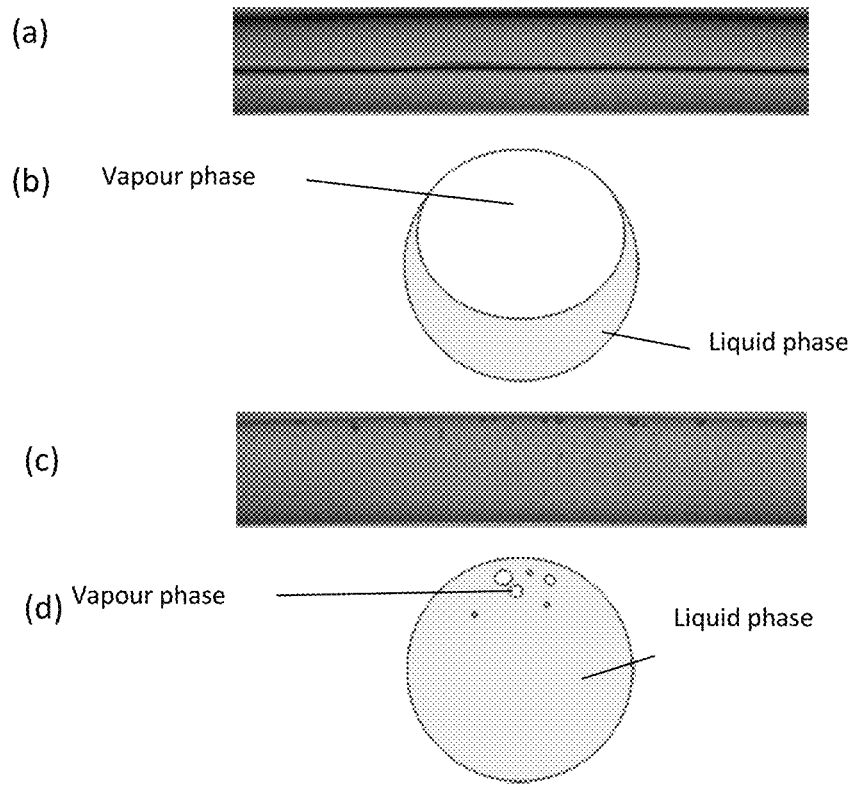
FIG. 9 illustrates interface structures for slug flow (parts a and c) and corresponding simplified multi-phase structures (parts b and d).
Figure 10:
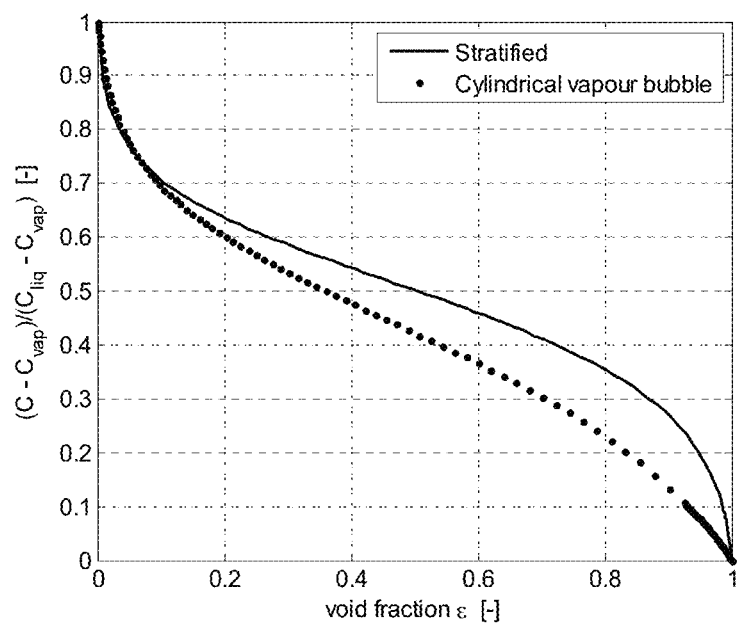
FIG. 10 illustrates FEM simulations for slug flow with a stratified and with cylindrical elongated vapour bubbles, as well as the corresponding assumed multi-phase structures (parts b and c)
Figure 10:
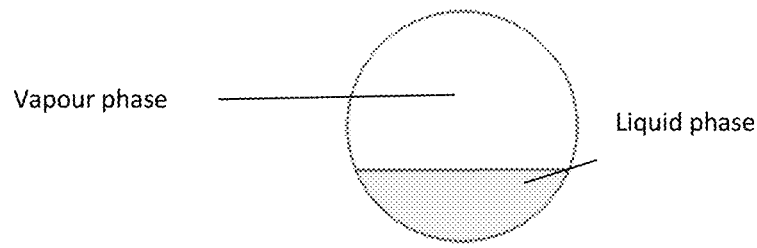
Figure 10:
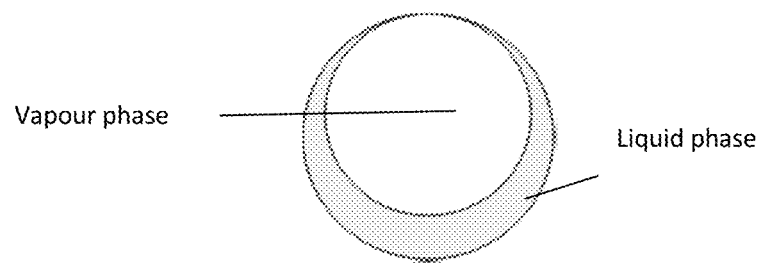

For slug flow, two multi-phase structures occur sequentially in time due to the occurrence of vapour bubbles as is shown for an 8 mm tube in FIG. 9. The first multi-phase structure corresponds to an elongated gas bubble as shown in FIG. 9 part (a) and a corresponding simplified spatial distribution of the phases in the cross section of the channel multi-phase structure is shown FIG. 9 part (b). This vapour bubble multi-phase structure alternates with a multi-phase structure consisting of a liquid slug with just a few vapour bubbles in them, this is shown in FIG. 9 part (c) and a corresponding simplified multi-phase structure in cross-section is shown FIG. 9 part (d). For the elongated bubble multi-phase structure, the shape of the elongated bubble is important to determine the relationship between the void fraction and the capacitance. At first two very simple assumptions for the multi-phase structure were compared: one where the liquid forms a stratified layer at the bottom of the tube (FIG. 10.B) and one where the vapour bubble is perfectly cylindrical (FIG. 10C). The C-ε relation for these cases was determined using FEM simulations and are shown in FIG. 10 (A). Both these calibration curves were used to determine a void fraction for each slug measurement, the results were compared to the Rouhani-Axelsson drift flux void fraction model and the homogeneous void fraction model. The agreement with the Rouhani-Axelsson model for the multi-phase structure of the cylindrical elongated bubble assumption (FIG. 10C) was very good.

For the multi-phase structure of the stratified bubble assumption (FIG. 10 B) the void fraction was systematically over estimated. Moreover, in more than 50% of the cases, the calculated void fraction for this assumption was larger than the homogeneous void fraction, which is not possible. As can be seen in FIG. 7 and FIG. 8, slug flow occurs at low vapour fractions. Yet when the multi-phase structure of an elongated vapour bubble is passing, the local void fraction can be quite high. This can also be seen in the obtained results discussed later in this description.

For the liquid slug, the multi-phase structure is mainly all liquid flow with just a few small vapour bubbles which are mostly quite close to the top wall of the tube. This can be seen in FIG. 10 part (a). For this multi-phase structure, the cylindrical vapour bubble assumption also gave good results. For other (not spherical) vapour bubble geometries the results were only marginally different from that for spherical ones. Hence, the C-ε relationship for the multi-phase structure of the cylindrical vapour bubbles can be used for determining the void fraction for both the elongated vapour bubbles as for the liquid slugs. The results of the calibration are shown in the next paragraph.

Intermittent Flow

Figure 11A:
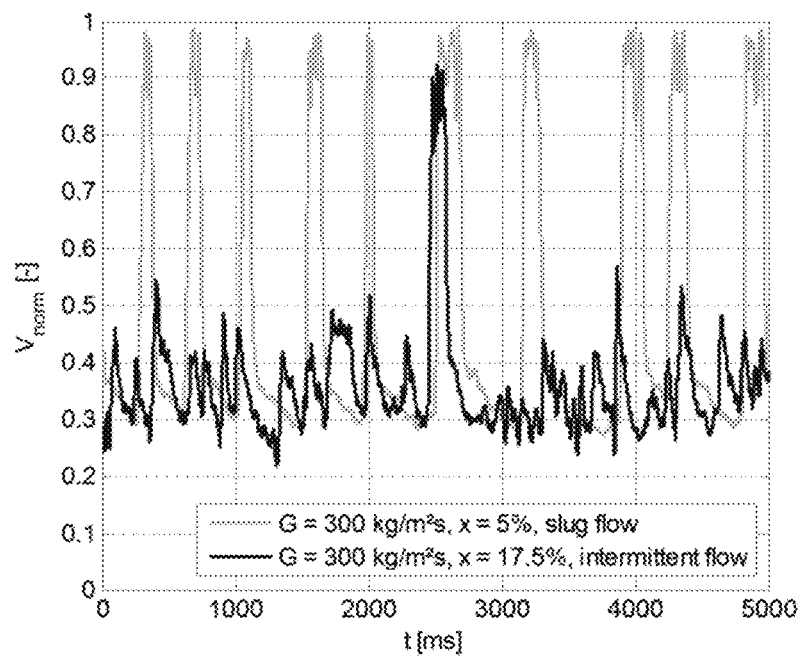
FIG. 11a and FIG. 11b illustrates the normalized sensor signal for different mass fluxes G and vapour fractions x values, illustrating features of embodiments of the present invention.
Figure 11B:
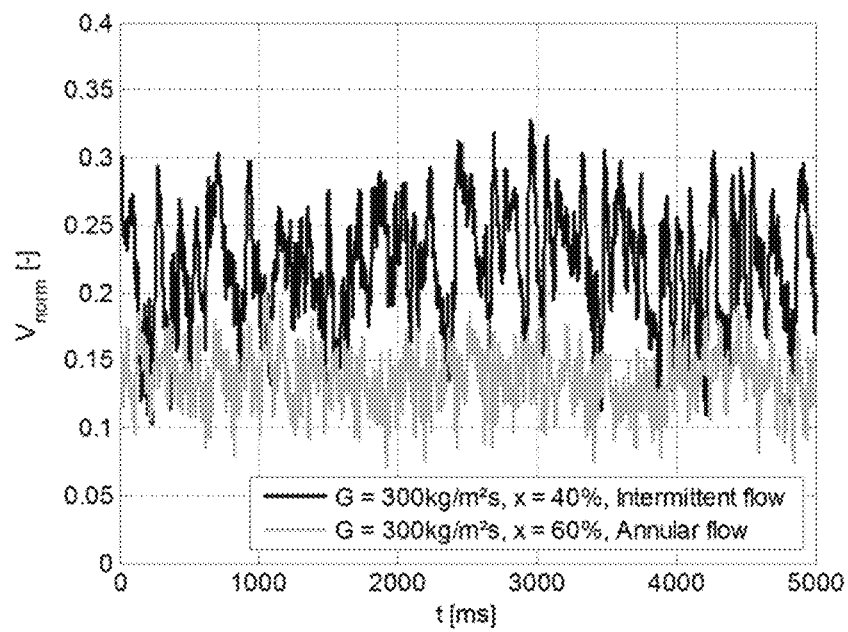

The interface structures for slug and annular flow are quite different from one another. Intermittent can be seen as a transitional flow regime between slug flow and annular flow. For low vapour fraction x, it shows a lot of similarity with slug flow. Liquid waves obstructing a large part of the tube cross section still occur, though they don't reach the top of the tube anymore. For higher x, the flow behaviour starts to look more and more like annular behaviour. This is illustrated in FIG. 11a and FIG. 11b where the normalised sensor signal for several vapour fraction x and mass flux G are shown. In FIG. 11a a signal for slug flow and one for intermittent flow at low x is shown, whereas FIG. 11b shows a signal for intermittent flow at high x and one for annular flow.

Because the intermittent multi-phase structure seems to be a transition between slug and annular flow and due to lack of other information regarding the structure of intermittent flow, the void fraction for this flow regime is determined as a weighted average of the void fraction for slug flow and that for annular flow. Three different weighting methods were tested and showed relatively good results:

Weighing Based on the Vapour Fraction:

$$\varepsilon_{intermittent} = (x - x_{IS}) \cdot \varepsilon_{slug} + (x_{IA} - x) \cdot \varepsilon_{annular} \quad (2)$$

In this equation $x_{IS}$ is the vapour fraction at which the slug-intermittent flow transition occurs and $x_{IA}$ is the vapour fraction at which the intermittent-annular transition occurs. For this method, $x_{IS}$ and $x_{IA}$ are determined using a flowmap. Two different flow maps were tested in the present example: the Wojtan-Ursenbacher-Thome flow map as described in International Journal of Heat and Mass Transfer 48 (2005) 2955-2969, and the intermittent-annular transition boundary by Barbieri et al. in "Flow patterns in convective boiling of R-134a in smooth tubes of several diameters" presented at the 5$^{th}$ European Thermal-Sciences Conference, The Netherlands 2008 combined with the slug-intermittent transition boundary of the Wojtan-Ursenbacher-Thome flow map. The last combination agreed best with the recorded dataset.

Weighing based on the vapour fraction as in the previous method, but $x_{IS}$ and $x_{IA}$ are determined from experimental results. For the expected G and x range a certain amount of measurement points need to be available. For each measurement from this dataset the flow regime was determined and a flow map for the measured data was plotted similar to FIG. 7 and FIG. 8. From this flowmap $x_{IS}$ and $x_{IA}$ could then be determined.

For the first two methods x and G need to be measured for each data point in order to perform the weighing. This might not always be a very practical requirement. Therefore, a method where the weighing is performed based on the same parameters as used to determine the flow regime, was envisaged. These parameters are the mean $\mu$, the variance $\sigma$ and a frequency parameter F95 (frequency for which 95% of the frequency spectrum is lower) of the measured sensor signal. The weighing is performed as follows:

$$\varepsilon_{intermittent} = \frac{((1-F95) \cdot \mu \cdot \sigma \cdot \varepsilon_{slug} + (1-\mu) \cdot (1-\sigma) \cdot F95 \cdot \varepsilon_{annular})}{((1-F95) \cdot \mu \cdot \sigma + (1-\mu) \cdot (1-\sigma) \cdot F95)} \quad (3)$$

Figure 12:
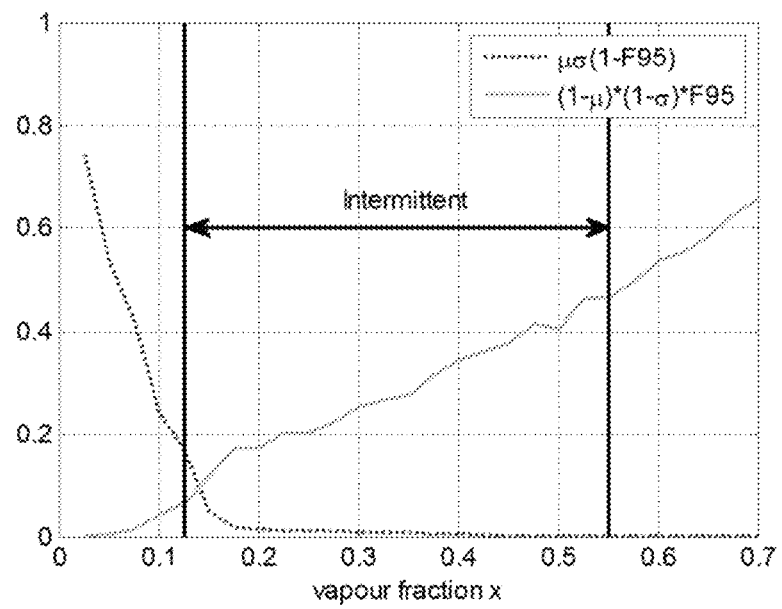
FIG. 12 shows the evolution of two parameters used for characterizing intermittent flow, as can be used in embodiments of the present invention.

In this, $\mu\sigma$ and F95 were normalized parameters for the entire dataset. For slug flow the sensor signal had a high average and variance and a low frequency parameter, for annular flow $\sigma$ and $\mu$ are low and F95 was high. This is depicted in FIG. 12 for R410A and G=300 kg/m$^2$s, whereby $\mu \cdot \sigma \cdot (1-F95)$ is high for low x (more slug-like flows) and $(1-\mu) \cdot (1-\sigma) \cdot F95$ is high for high x (more annular-like flows).

Annular Flow

Figure 13:
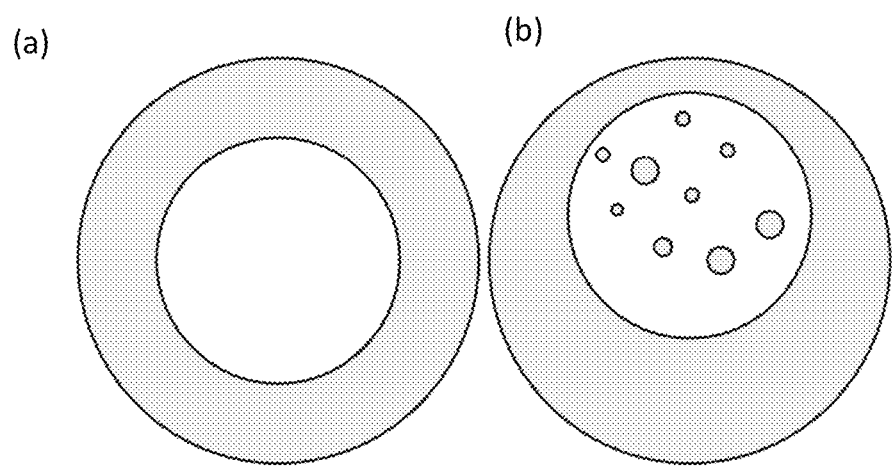
FIG. 13 illustrates two simplified flow liquid-vapour interface structures for annular flow, as can be used in embodiments according to the present invention.

FIG. 13 part (a) shows the single simplified multi-phase structure for annular flow: a liquid ring with a vapour core in the middle. Yet, this is not a very realistic multi-phase structure. In the vapour core, liquid droplets of various sizes can be entrained. Also, for horizontal tubes the liquid film tends to be thicker at the bottom of the tube due to gravity. A more realistic (though exaggerated) annular multi-phase structure is shown in FIG. 13 part (b). It goes without saying that to perform an adequate calibration, a realistic multi-phase structure should be assumed when determining the C-$\varepsilon$ curve. Yet, this is only necessary if the C-$\varepsilon$ relation for the realistic multi-phase structure differs significantly from that for a simplified multi-phase structure.

Figure 14:
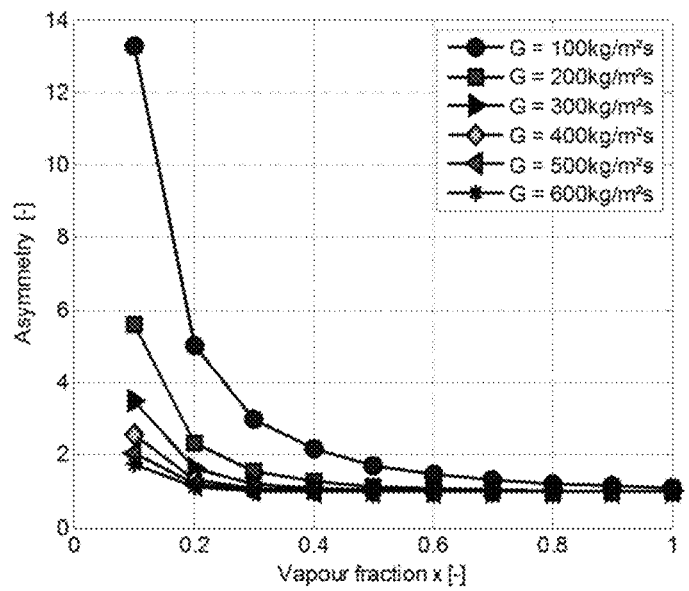
FIG. 14 illustrates asymmetry of an annular liquid film, as can be taken into account in embodiments according to the present invention.

The effect of gravity on the annular multi-phase structure can be expressed as the asymmetry of the liquid film; this is defined as the ratio of the liquid film thickness at the bottom $\delta_{bottom}$ and the liquid film thickness at the top $\delta_{top}$. In FIG. 14 the asymmetry of the liquid film for a refrigerant R134a at a temperature of 15° C. and in a tube with diameter 8 mm is shown as calculated with the correlation of Schubring et al. in International Journal of Multi-phase Flow 35 (2009) 389-397. Comparing this to the data shown in FIG. 7, one can clearly see that the asymmetry is always lower than 3 for a G and x where the flow regime is annular. The results for R410A are not shown here, but for this case the asymmetry is also limited to 3.

Figure 15:
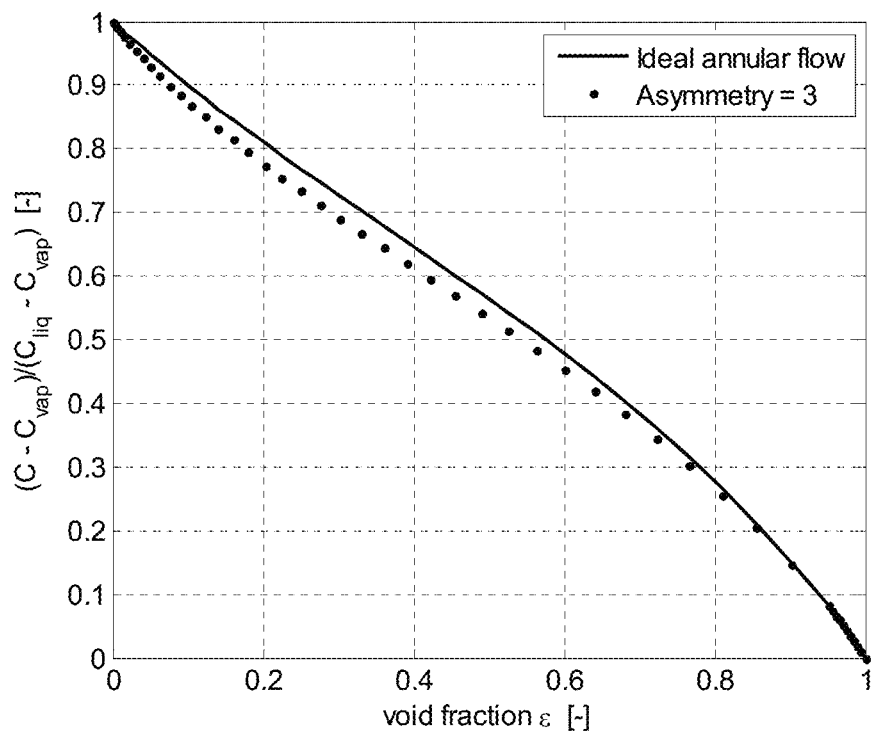
FIG. 15 illustrates the effect of asymmetry of a liquid film on the normalized calibration curve, as can be taken into account in embodiments according to the present invention. The asymmetry was determined as described in International Journal of Multi-phase Flow 35 (2009) 389-397.

In FIG. 15 the effect of the assymetry of the liquid film on the normalized calibration curve (i.e. the C-□ relationship) is shown. For annular flow the void fraction is typically large, in FIG. 19 and FIG. 20 further on it can be observed that the minimum void fraction for annular flow is 80%. For these high void fractions the effect of the assymetry of the film is small to negligible. Next, the correlation of Oliemans et al. as described in International Journal of Multi-phase Flow 12 (1986) 711-732 is used to determine the entrained fraction. The entrained fraction e is defined as the ratio of the mass flow rate of droplets in the gas core $m_{drop}$ to the total liquid mass flow rate $m_{liq}$. The maximum droplet hold up $\gamma$ can now be estimated by neglecting the slip between the gas phase and the liquid droplets, thus assuming they are small enough to follow the gas flow rather than suffer from their inertia:

$$\gamma = e \frac{\varepsilon}{1-\varepsilon} \frac{1-x}{x} \frac{\rho_g}{\rho_l} \quad (4)$$

Figure 16:
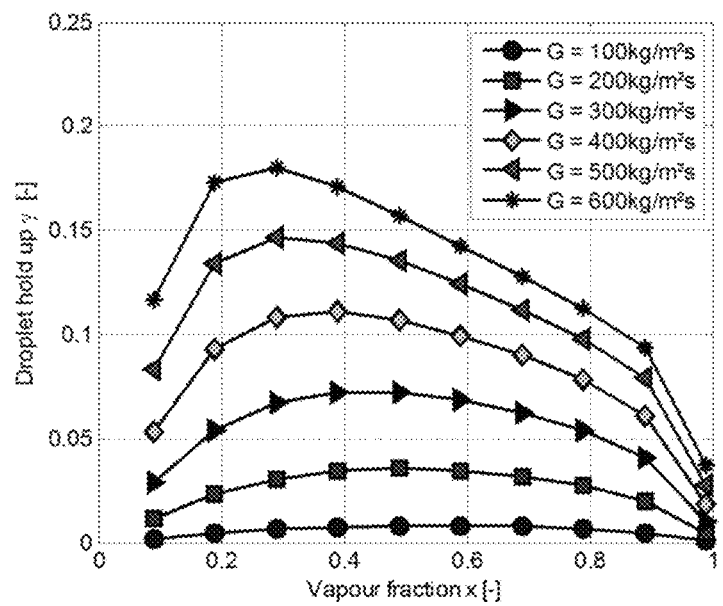
FIG. 16 illustrates the droplet hold up in the vapour core during annular flow, as can be taken into account in embodiments according to the present invention. The droplet hold up in the vapour core was calculated as described in International Journal of Multi-phase Flow 36 (2010) 293-302.
Figure 17:
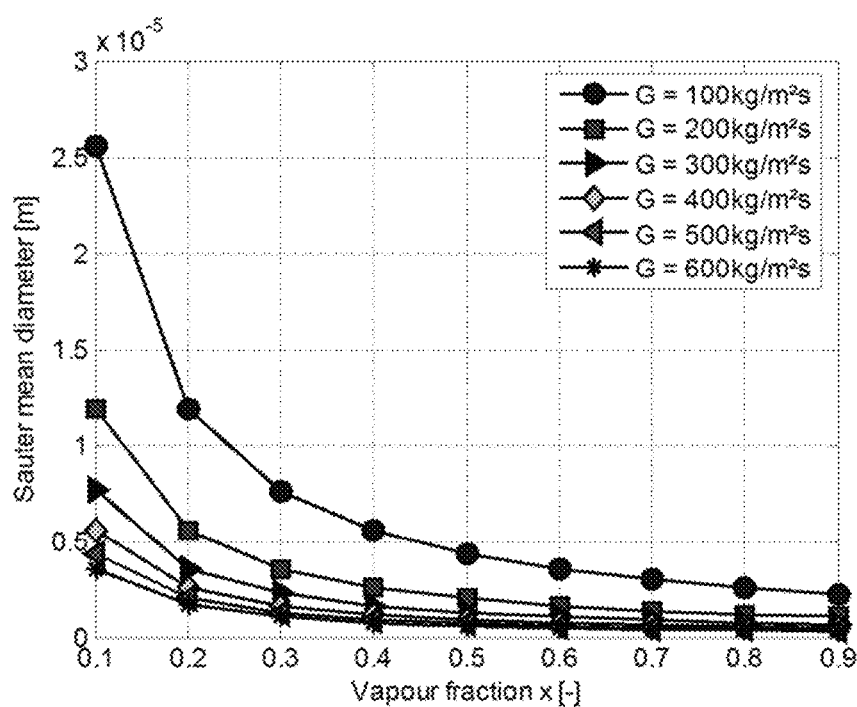
FIG. 17 shows the sauter mean diameter of the entrained droplets in a vapour core during annular flow, as can be taken into account in embodiments according to the present invention. The sauter mean diameter was calculated as described in International Journal of Multi-phase Flow 23 (1997) 1-53.

In equation (4) the void fraction $\varepsilon$ is determined with the Rouhani-Axelsson drift flux void fraction model. FIG. 16 shows the predicted droplet hold up for R134a at 15° C., one can see that $\gamma$ is limited to 0.2 for all mass fluxes. For the sake of simplicity, the droplet hold up for other temperatures and for R410A are not shown here, though they are all limited to 0.2. The sauter mean diameter of the entrained droplets can be determined, the results for R134a being shown in FIG. 17. Comparing this with FIG. 17 one can see that the Sauter mean diameter of the droplets is mostly in the order of 2 $\mu$m. The result for R410A are not shown here for simplicity, but they are entirely similar. As a result for both refrigerants, the Sauter mean diameter of the entrained droplets for annular conditions does not seem to be influenced much by G or x. Yet, the droplet hold up $\gamma$ does vary quite a lot with G and x. If the effect of the entrained droplets would be accounted for in the calibration curves, this would make the calibration quite dependent of G, x and the correlations that are used to predict the entrained fraction. This means that in order to use the proposed measurement technique, G and x need to be measured as well. This limits the flexibility of the measurement technique for e.g. offshore monitoring of multi phase streams. Therefore, as a first approximation, the annular interface is assumed to be a perfect circular ring structure as depicted in FIG. 13 part (a) without considering the entrainment. As will be discussed further on, this approximation yields quite good results for the low mass fluxes, where the droplet hold up is limited. For higher mass fluxes the approximation leads to a slight over estimation of the void fraction.

Experimental Results

Figure 18A:
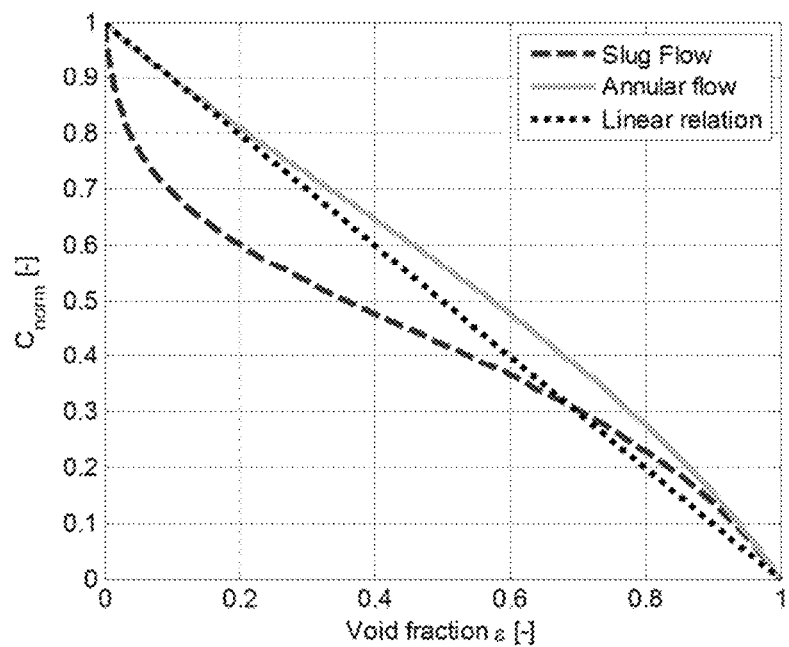
FIG. 18a and FIG. 18b illustrates the calibration curves for R134a and R410A and for comparison non-calibrated data (linear relation), as can be used in embodiments of the present invention.
Figure 18B:
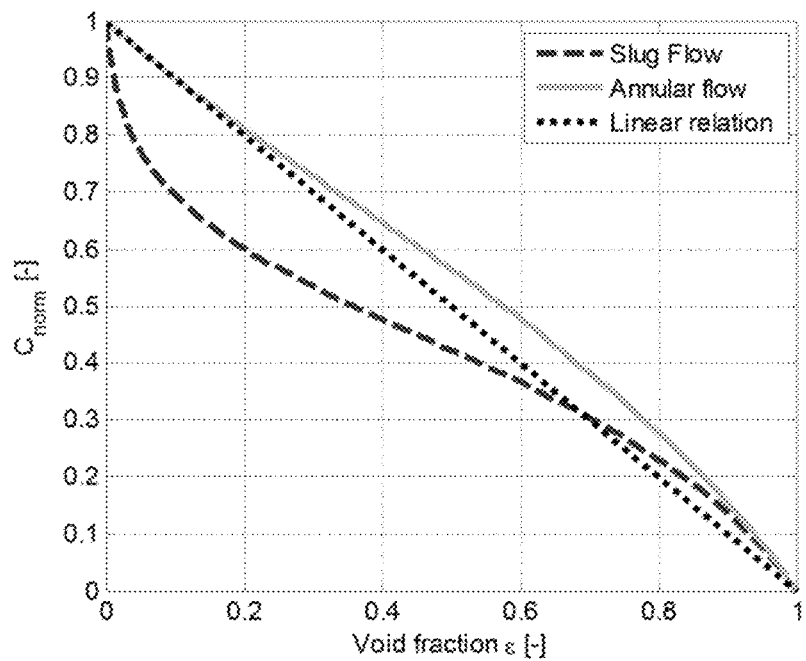
Figure 19A:
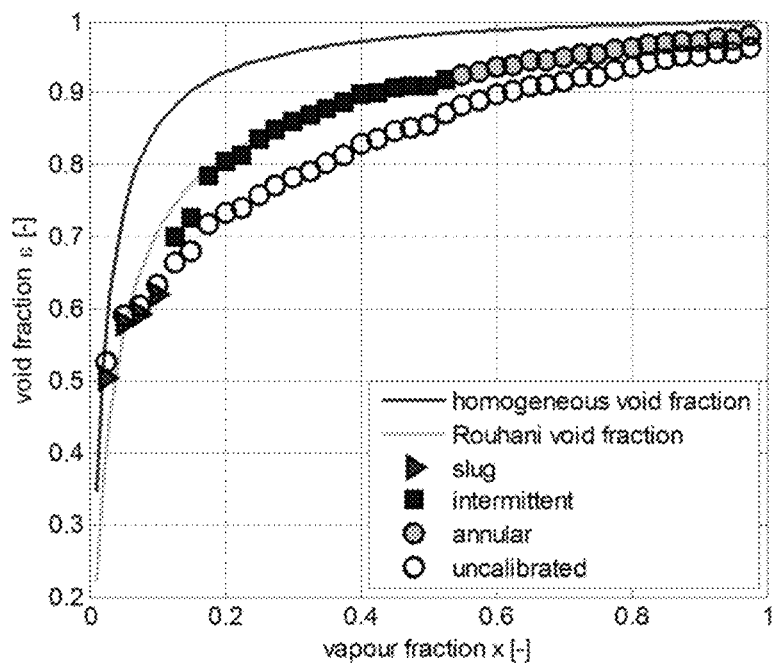
FIG. 19a to FIG. 20d illustrate calibration results for refrigerant R134a (FIG. 19) and refrigerant R410A (FIG. 20) for a mass flux G of 200 kg/m²s (FIG. 19a, FIG. 20a), 200 kg/m²s (FIG. 19b, FIG. 20b), 200 kg/m²s (FIG. 19c, FIG. 20c) and 200 kg/m²s (FIG. 19d, FIG. 20d), illustrating features of embodiments of the present invention.
Figure 19B:
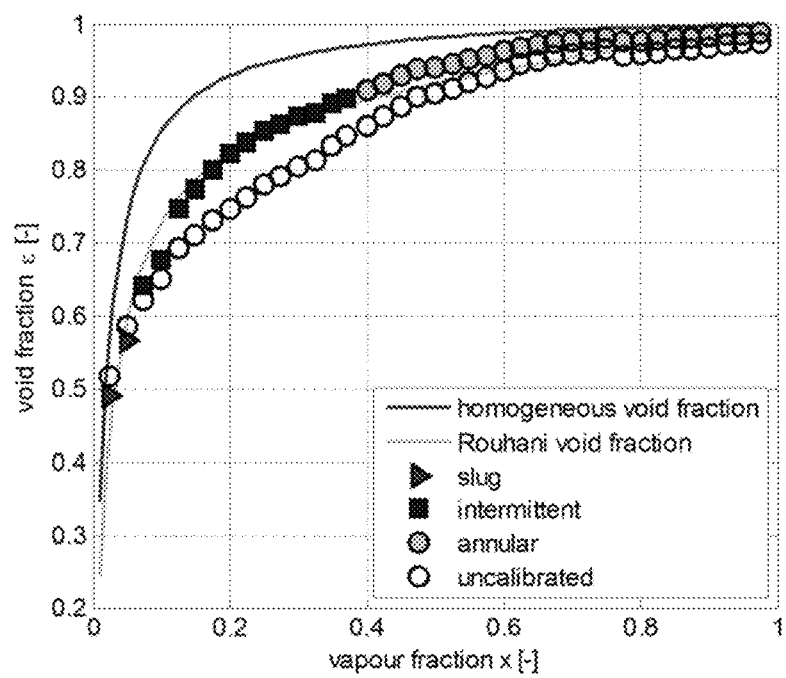
Figure 19C:
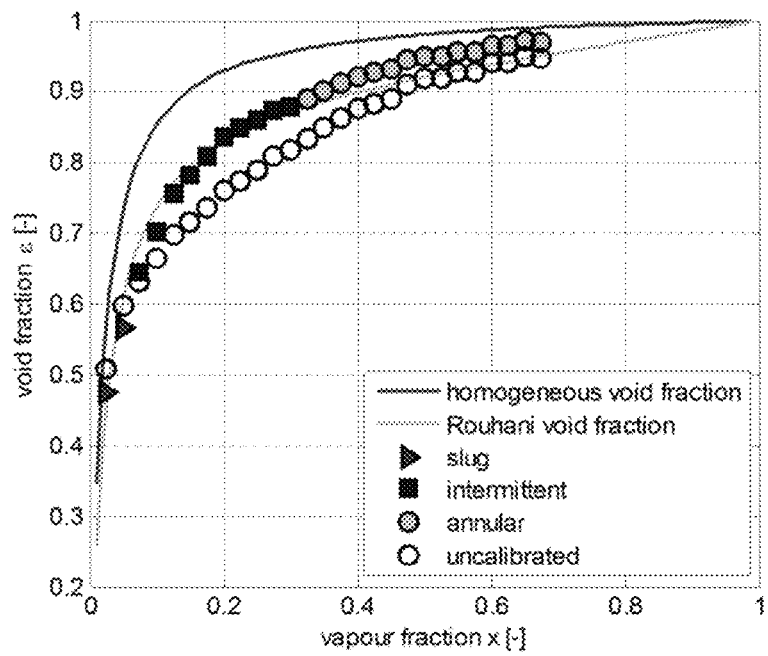
Figure 19D:
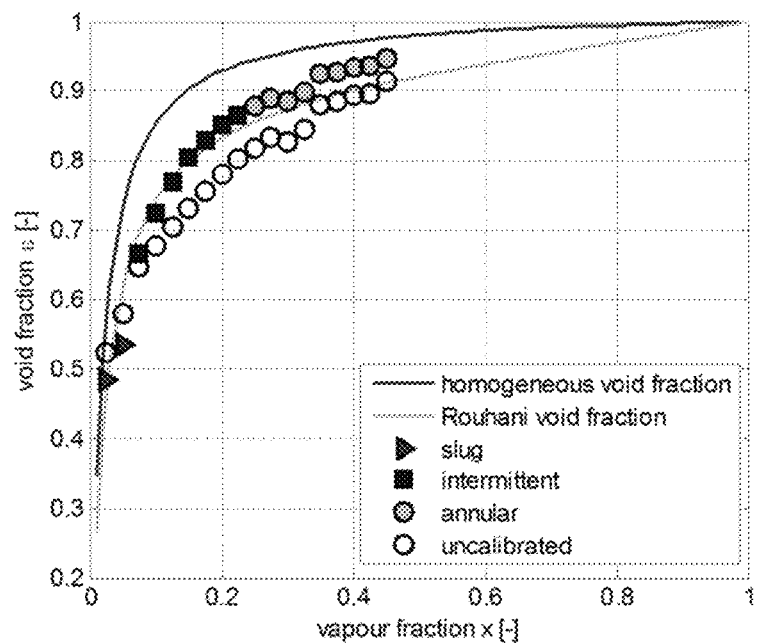
Figure 20A:
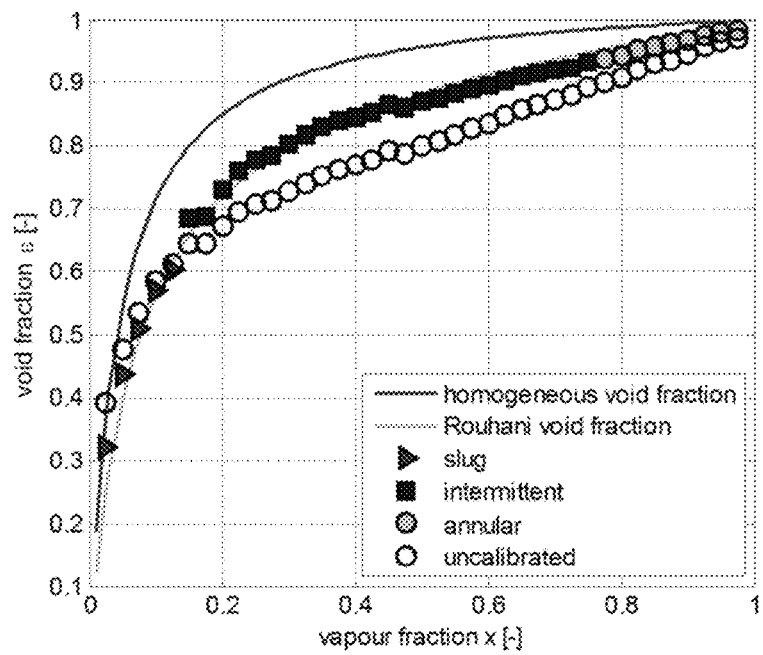
Figure 20B:
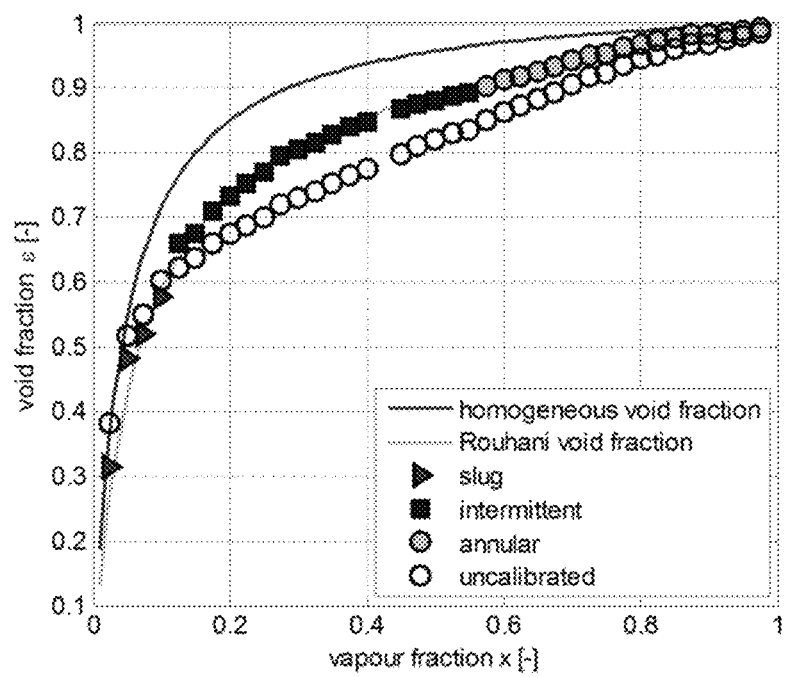
Figure 20C:
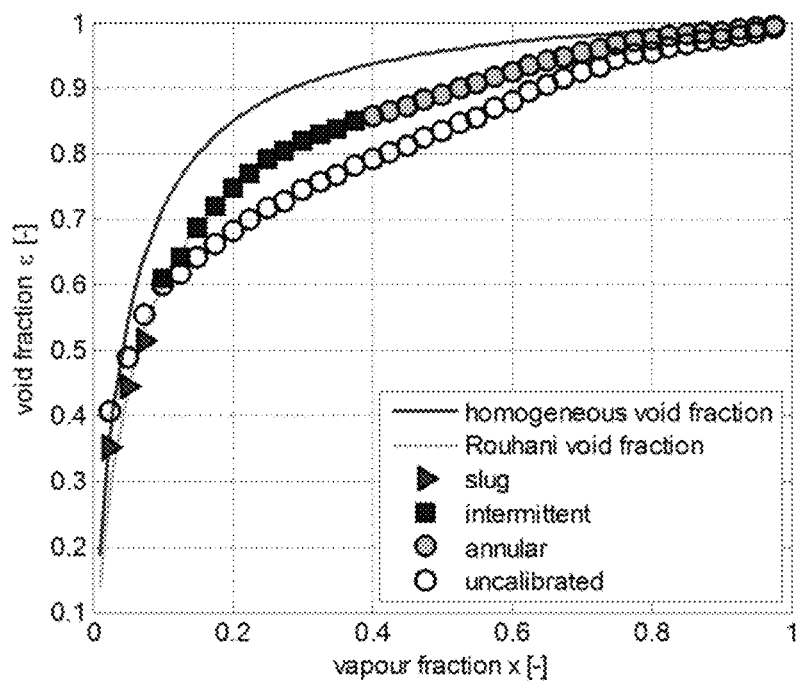
Figure 20D:
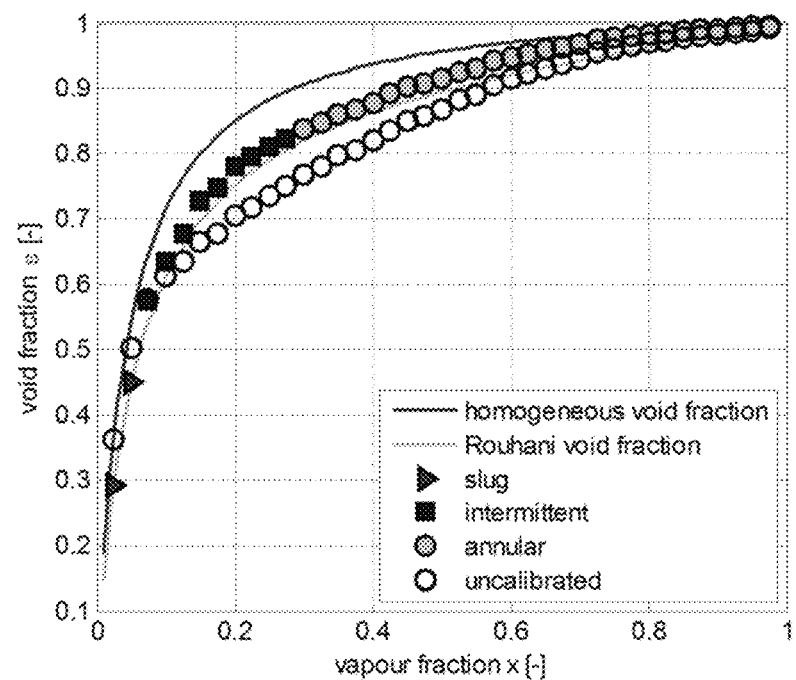

In the following, the results obtained using a method according to embodiments of the present invention are discussed. A set of calibration curves for R410A and R134a based on the principles discussed above are shown in FIG. 18a and FIG. 18b respectively. From these curves it is clear that method and device according to the present invention allows for a more accurate determination of the void fraction, compared to prior art methods and devices by determining the void fraction using the C-ε curve(s) of the previously obtained flow regime. Not taking into account the flow regime may lead to an error for the capacitance of 30% or more as can be derived for instance from FIG. 18b. The results of the calibration are shown in FIG. 19a to FIG. 19d for R134a and in FIG. 20a to FIG. 20d for R410A. For these figures the weighing for intermittent flow was based on the vapour fraction and $x_{IS}$ and $x_{IA}$ are determined from measurements. For the uncalibrated results, a linear relationship between capacitance C and dielectric constant E is assumed. The results for the other weighing methods are not shown here, but they are compared in table 1. The different weighing methods are thereby compared to the Rouhani-Axelsson drift flux void fraction model. Method 1 thereby is a weighing technique whereby $x_{IS}$ and $x_{IA}$ are determined from measurements, method 2 thereby is a weighing technique whereby $x_{IS}$ and $x_{IA}$ are determined from flowmaps, and method 3 thereby is a weighing technique based on parameters for clustering It is observed that each method gives a quite similar result. The actual choice of the method to use can therefore mainly depend on practical considerations.

Whereas FIG. 19 and FIG. 20 illustrate the results for the time averaged void fraction, the void fraction in practice varies in time. This is very pronounced for slug flow and intermittent flow. The Rouhani-Axelsson drift flux void fraction model might predict the average void fraction very well; it cannot predict the dynamic behaviour of the void fraction. This can be measured using the capacitive void fraction sensor according to embodiments of the present invention. The effect of the calibration on the sensor signal is therefore now discussed for every flow regime.

Figure 21A:
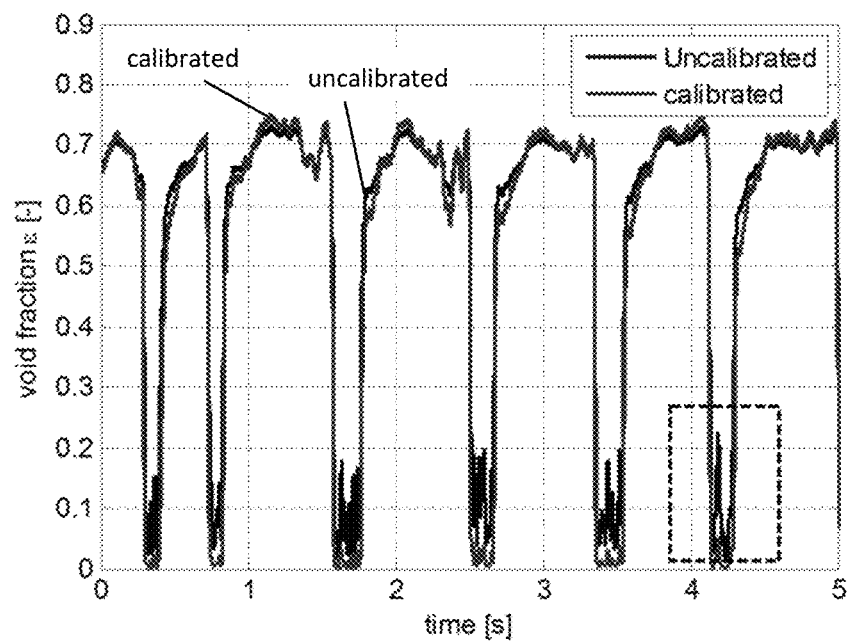
FIG. 21a and FIG. 21b (detail of FIG. 21a) illustrates a comparison of a non-calibrated and a calibrated signal for slug flow, illustrating features and advantages of embodiments of the present invention.
Figure 21B:
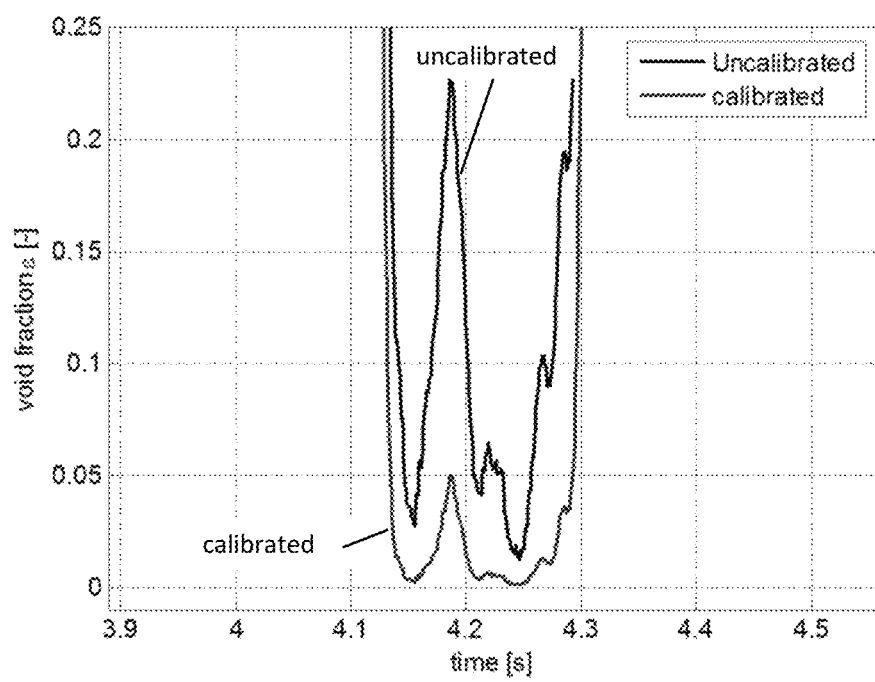

FIG. 21a shows the uncalibrated (linear C-ε relation assumed) and the calibrated signal for slug flow. For the uncalibrated data a linear C-ε relation is assumed because if the sensor plates and channel would be straight, the measured capacitance would not be dependent on the flow regime and the C-ε relation would indeed be linear. The refrigerant used is R410A, with G=300 kg/m$^2$s and x=7.5%. As can be seen, the diversion from the uncalibrated signal (no flow regime dependence of the C-ε signal assumed) is the largest for low void fractions. This can also be seen above (FIG. 18A en FIG. 18B) where it is shown that the normalized C-ε curve differs the most from a linear relation for small void fractions. Which means that here the flow regime dependence effect is larger. In the close up shown in FIG. 21b the effect is depicted more clearly. By assuming a linear C-ε relation, the void fraction for the liquid slugs is strongly over estimated. As described above, there are only a few small vapour bubbles present in the liquid slugs, which clearly does not amount to a void fraction of 20%.

Figure 22:
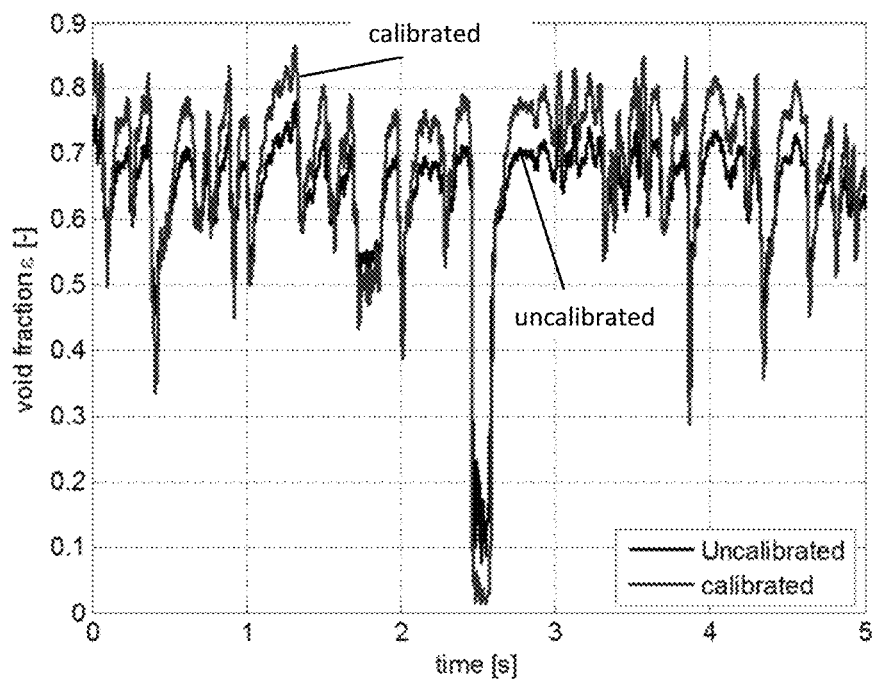
FIG. 22 illustrates a comparison between the void fraction determined using an non-calibrated signal and a calibrated signal for intermittent flow, illustrating features and advantages of embodiments of the present invention.

As can be seen in FIG. 19 and FIG. 20 assuming a linear C-ε relation leads to an underestimation of the void fraction for intermittent flows. Calibration leads to a higher average void fraction. The latter is also illustrated in FIG. 22, for the example of a fluid being R410A at intermittent flow, G=300 kg/m$^2$, x=15%.

Figure 23:
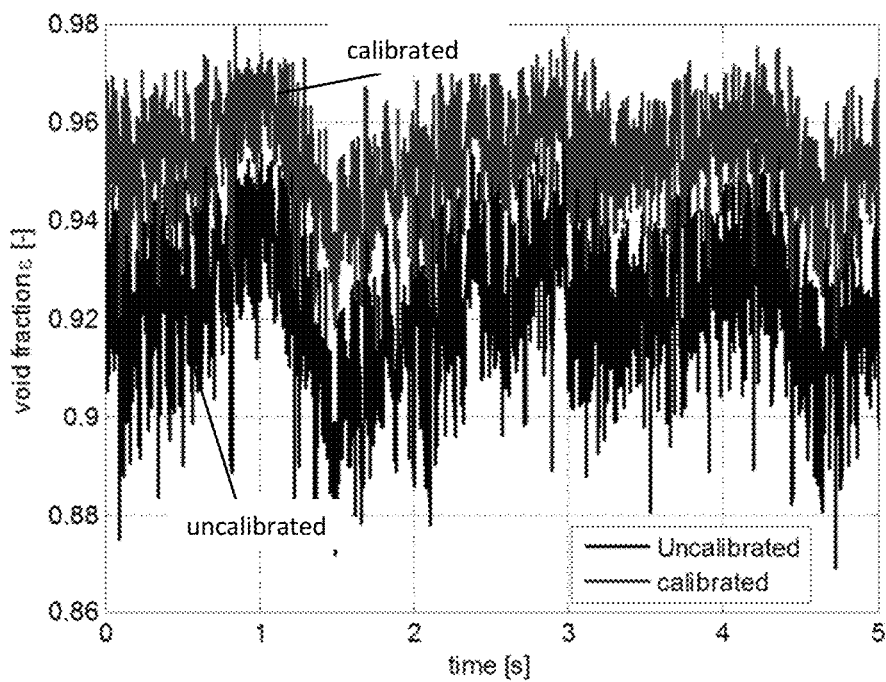
FIG. 23 illustrates a comparison between the void fraction determined using a non-calibrated signal and a calibrated signal for annular flow, illustrating features and advantages of embodiments of the present invention.

Assuming a linear C-ε relation leads to an underestimation of the void fraction for a part of the annular measurement points. As can be seen in FIG. 19 and FIG. 20 this is mainly the case for low mass fluxes and relatively low vapour fractions. In FIG. 23 the result of the calibration is compared to assuming a linear C-ε relation for x=75%, G=300 kg/m$^2$s and R410A. It is clear that for a calibrated case the average void fraction is higher than for the uncalibrated case.

In another aspect, the present invention relates to systems using slurries. A slurry is a fluid mixture of a pulverized solid

TABLE 1

|  | method 1 | | method 2 | | | | method 3 | |
|---|---|---|---|---|---|---|---|---|
|  | | | Thomeflowmap | | Barbieriflowmap | | | |
|  | μ (%) | σ (%) | μ (%) | σ (%) | μ (%) | σ (%) | μ (%) | σ (%) |
| R410A, Slug flow | 4.514 | 10.227 | 1.7492 | 10.68 | 1.7492 | 10.68 | 7.062 | 10.2258 |
| R410A, Interm. flow | 0.224 | 1.804 | 2.0793 | 3.5878 | 2.0824 | 4.3032 | 1.3837 | 3.623 |
| R410A, Annular flow | 0.806 | 1.260 | 0.2731 | 1.6120 | 0.5477 | 1.4775 | 0.8211 | 1.2896 |
| R410A, Total | 0.905 | 3.508 | 1.0652 | 4.6661 | 1.1539 | 4.7400 | 1.6077 | 4.1477 |
| R134a, Slug flow | −2.356 | 12.253 | −3.6619 | 9.3178 | −3.6619 | 9.3178 | −0.1181 | 9.662 |
| R134a, Interm. Flow | −0.8266 | 2.381 | 0.4864 | 1.8933 | −0.297 | 1.2539 | −0.1223 | 1.3649 |
| R134a, Annular flow | 1.332 | 1.332 | 1.218 | 1.5783 | 1.3919 | 1.4756 | 1.3365 | 1.6126 |
| R134a, Total | 0.19 | 4.02 | 0.1529 | 4.4432 | 0.1171 | 4.397 | 0.6433 | 2.97 | with a liquid; slurries can flow in both steady and unsteady flow regimes. These slurries can then be pumped to e.g. use for cooling or just as a convenient way to displace solids in bulk. One or multiple sensors could be used in the production of the slurry or to monitor the quality of the slurry. Since the sensor signal can be used to determine the fluid/solid ratio of the slurry. A specific example in the use of the sensor for making/monitoring slurries are ice slurries. These slurries can be used as a cooling fluid in cooling systems. The specific advantage of these slurries is that the moment of production and the moment of usage do not need to coincide as is the case for a classical vapour-compression systems. These ice slurries can hence be used as a means of energy storage. However in the production process of these slurries and the usage as a cooling fluid, the amount of liquid/vapour/solid present is essential to the quality of the produced slurry and the cooling performance. Since the vapour phase, liquid phase and solid phase have different dielectric constants, the amount of each phase can be determined.

In another aspect, the present invention relates to a heat transfer system. More particularly, to the detection of fouling in a heat transfer system. Fouling is the accumulation of unwanted material on solid surfaces to the detriment of function. For example, if the operating fluid is water, scale can form on the surface of the heat transfer system, reducing the heat transfer. Fouling mostly builds up over a matter of time and common practice is to periodically clean the heat transfer system to remove the fouling. The time between these cleaning interventions is mostly based on experience and rule of thumb. The present invention can be used to monitor the fouling and decide whether cleaning is necessary or not. One or multiple sensors can be used since the fouling and the working fluid have a different dielectric constant, the thickness and shape of the fouling layer can be monitored. Hence, the operating time of the heat transfer system is maximized since the system will only be shut down if necessary and not on fixed moments.

In another aspect, the present invention relates to a heat transfer system, more particularly a heat transfer system designed or controlled to have good operation. The heat transfer system according to embodiments of the present invention comprises a distributor, a plurality of parallel circuits of flow channels and a collector, combining the plurality of parallel circuits of flow channels of the heat transfer system. In this way, the output substance flow of each of the parallel circuits is recombined. The distributor is arranged for (upstream the collector) distributing an incoming substance flow over a plurality of parallel circuits.

According to embodiments of the present invention, the heat transfer system comprises a valve for controlling the flow through a flow channel of at least one circuit. Advantageously, a valve may be present in more or—more advantageously—in each of the circuits of the set of parallel circuits of the heat transfer system. The valve or valves may be arranged such that they are controllable as function of a void fraction of a substance in the at least one circuit. Furthermore, the valve or valves may be adapted for controlling the flow, e.g. the flow type and the different fractions such as fluid, vapour, etc. . . . being present in the substance, through a flow channel of one circuit. Advantageously, the heat transfer system also comprises at least one sensor in the at least one circuit for sensing a void fraction dependent parameter of the substance flowing through the flow channel and a controller for controlling the valve in the at least one circuit as function of a void fraction dependent parameter sensed.

Figure 24:
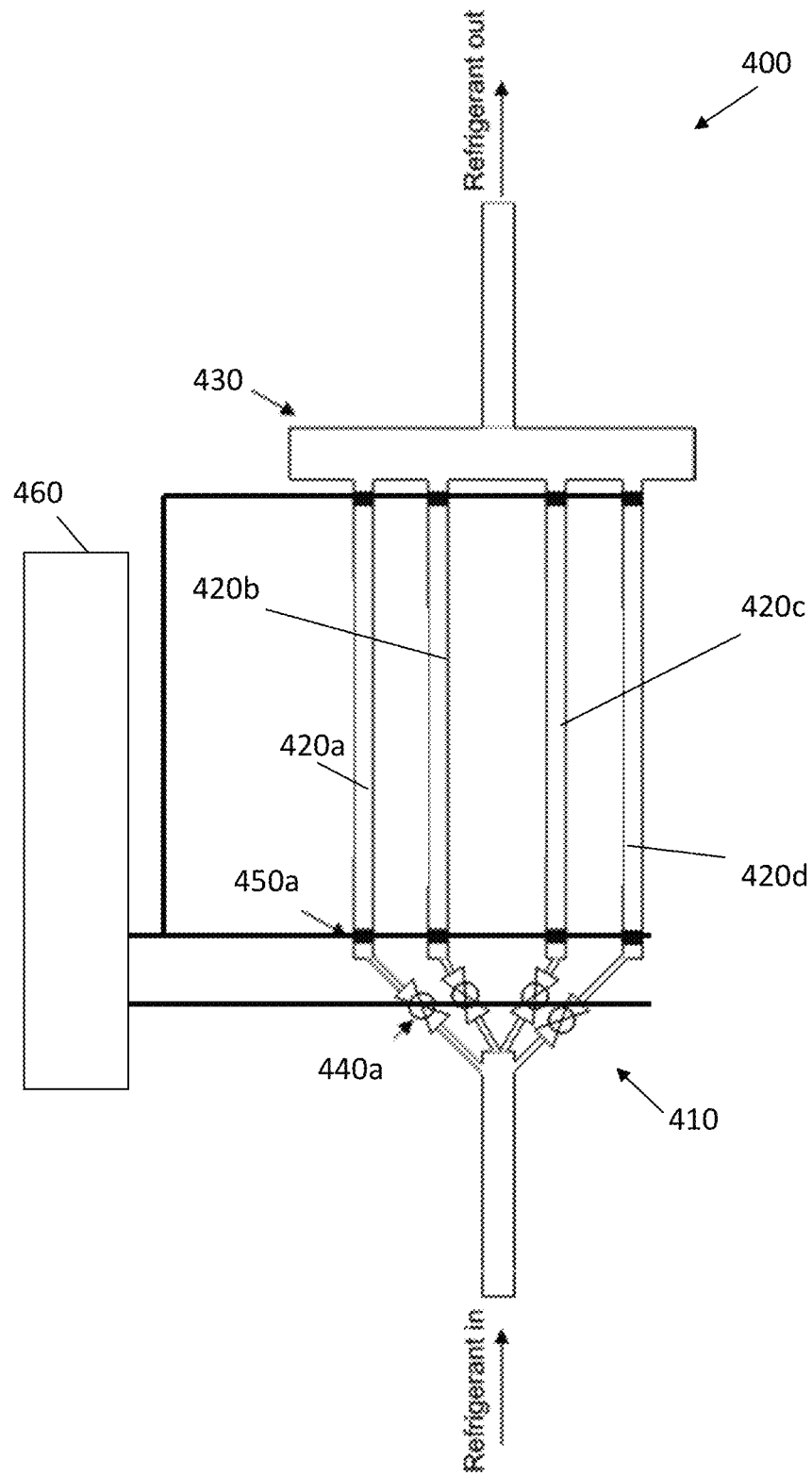
FIG. 24 illustrates a heat transfer system with valve control according to an embodiment of an aspect of the present invention.

By way of illustration, embodiments of the present invention not being limited thereto, an example of a system according to an embodiment of the present invention is shown in FIG. 24. illustrates part of an exemplary heat transfer system. The heat transfer system 400 comprises a distributor 410. The distributor 410 distributes an incoming flow, e.g. of refrigerant, to a set of parallel circuits 420a, 420b, 420c, 420d, . . . . The parallel circuits 420a, 420b, 420c, 420d, are combined again to re-obtain a single flow of the refrigerant in a collector 430. The heat transfer system furthermore comprises a valve 440 in each of the circuits of the set of parallel circuits and at least one sensor 450, in the current example being one sensor at the start of the circuit and one sensor at the end of the circuit, for each of the circuits. The sensors thereby are adapted for determining a void fraction dependent parameter. The heat transfer system furthermore comprises a controller 460, adapted for controlling the valves in each of the circuits, dependent on the void fraction dependent parameter sensed. The valves may be controlled, e.g. based on a feedback control loop, in such a manner that at least one of the circuits comprises a substance only having an evaporated fraction at the outlet of the at least one circuit, in a manner that the evaporated fraction at the outlet is substantially the same for a group or for each of the circuits, or in a manner that there is variability between the evaporated fraction at the outlet of the different circuits. The controller may be programmed for performing a method as described in the first aspect of the present invention.

The heat transfer system or components thereof, e.g. the controller and/or the sensor, may comprise features and advantages of corresponding features in systems described in other aspects of the present invention.

It is an advantage of at least some embodiments according to the present invention that an automated and/or automatic control of a heat transfer system can be obtained.

In another aspect, the present invention also relates to a controller for controlling a heat transfer system as described above. Such a controller may comprise features and advantages of controllers described in similar or other aspects described in the present description. For example, the controller may be computer-implemented and may comprise similar features as described above for computer-implemented components.

In one aspect, the present invention also relates to a method of designing and/or controlling a heat transfer system. Such a method typically comprises the steps of, for at least one circuit of a set of parallel circuits of the heat transfer system, obtaining a void fraction dependent parameter of a substance flowing through the at least one circuit and controlling a valve in at least on circuit of the set of parallel circuits so as to induce a flow in the at least one circuit that only has an evaporated fraction of the substance in the circuit at the position where the at least one circuit is combined with other parallel circuits, the controlling taking into account the obtained void fraction dependent parameter or a void fraction determined based thereon. Alternatively or in addition thereto, the method may comprise controlling a valve in at least one circuit of a set of parallel circuits of the heat transfer system so as to obtain an identical evaporation state in more or each of the parallel circuits, the controlling taking into account the obtained void fraction dependent parameter or a void fraction determined based thereon. Alternatively, the method may comprise controlling a valve in at least one circuit of a set of parallel circuits of the heat transfer system so as to obtain a variable evaporation state of more or each of the parallel circuits, the controlling taking into account the obtained void fraction dependent parameter or a void fraction determined based thereon.

Further features and advantages of such a method may be as described elsewhere in this description. In one embodiment for example, a method may be applied for determining a void fraction of the substance flowing in the parallel circuits of the heat transfer system, e.g. near the outlet of the circuits, corresponding with the method as described in the first aspect of the present invention.

The invention claimed is:

1. A method of designing or controlling a heat transfer system comprising a set of at least two parallel circuits, the method comprising:
    obtaining, for at least one of the circuits of the set of parallel circuits, a void fraction dependent parameter of a substance being a multi-phase system flowing through the at least one circuit, and
    controlling a valve in at least one circuit of the set of parallel circuits
        so as to induce a flow in the at least one circuit that only has an evaporated fraction of the multi-phase system in the circuit at a position where the at least one circuit is combined with other parallel circuits or
        so as to obtain an identical evaporation state in more or each of the parallel circuits or
        so as to obtain a variable evaporation state of more or each of the parallel circuits,
    wherein the controlling of the valve is based on the obtained void fraction dependent parameter or a void fraction based on the void fraction dependent parameter.

2. A method according to claim 1, wherein obtaining a void fraction dependent parameter comprises sensing a void fraction dependent parameter.

3. A method according to claim 2, wherein obtaining a void fraction dependent parameter comprises determining the void fraction using a further method comprising:
    measuring a void fraction dependent parameter of the multi-phase system;
    obtaining a flow regime of the multi-phase system, said obtaining a flow regime comprising obtaining at least one multi-phase structure characteristic for the flow regime;
    obtaining a set of one or more relationships, specific for the obtained flow regime, between the void fraction dependent parameter and the void fraction, each of the relationships within one set corresponding to each of the obtained at least one multi-phase structures characteristic for the obtained flow regime;
    determining an occurring multi-phase structure;
    determining the void fraction of the multi-phase system based on the relationship between the void fraction dependent parameter and the void fraction for the determined occurring multi-phase structure.

4. A method according to claim 1, wherein the method comprises controlling operation of the heat transfer system based on the obtained evaporation state for one, more or advantageously all of the parallel circuits of the heat transfer system.

5. A controller for controlling a heat transfer system, the controller being programmed for performing a method according to claim 1.

6. A controller according to claim 5, the controller being implemented as a computer program product for performing, when executed on a processing means, the steps of the method according to claim 1.

7. A heat transfer system, the system comprising:
    a distributor:
    a plurality of parallel circuits of flow channels; and
    a collector,
    wherein the distributor is arranged for distributing an incoming substance flow, the substance being a multi-phase system, over the plurality of parallel circuits and the parallel circuits are combined in the collector for combining an output substance flow of each of the parallel circuits, and
    wherein the heat transfer system further comprises at least one valve for controlling the flow through a flow channel of at least one circuit, the at least one valve being controllable as function of a void fraction of the multi-phase system in the at least one circuit.

8. A heat transfer system according to claim 7, wherein the valve is adapted for controlling the flow through a flow channel of one circuit.

9. A heat transfer system according to claim 7, wherein the at least one valve is a valve for each of the circuits individually.

10. A heat transfer system according to claim 7, the heat transfer system comprising at least one sensor in at least one of the plurality of circuits for sensing a void fraction dependent parameter of the substance flowing through the flow channel.

11. A heat transfer system according to claim 7, the system comprising a controller for controlling the at least one valve as function of a void fraction dependent parameter of the substance flowing through a flow channel of the circuit, the flow being controlled by the at least one valve.

12. A heat transfer system according to claim 11, wherein the controller is part of a feedback control loop.

13. A heat transfer system according to claim 7, the system comprising a controller for controlling the at least one valve so as to induce a flow in the at least one circuit so as to obtain an identical evaporation state in more or each of the parallel circuits at a position where the parallel circuits are combined.

14. A heat transfer system according to claim 13, wherein the controller is part of a feedback control loop.

15. A heat transfer system according to claim 7, the system comprising a controller for controlling on/off operation of the heat transfer system, based on the obtained evaporation state for at least one circuit.

16. A heat transfer system according to claim 15, wherein the controller is part of a feedback control loop.

* * * * *